US012102389B2

(12) United States Patent
Toth et al.

(10) Patent No.: US 12,102,389 B2
(45) Date of Patent: Oct. 1, 2024

(54) EN FACE RETINAL VESSEL SHADOW VIEW OPTICAL COHERENCE TOMOGRAPHY IMAGES

(71) Applicant: Duke University, Durham, NC (US)

(72) Inventors: Cynthia Toth, Durham, NC (US); Kai Seely, Durham, NC (US); Vincent Tai, Durham, NC (US); Stephanie Chiu, Durham, NC (US); Katrina Winter, Durham, NC (US); Ryan Imperio, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 21 days.

(21) Appl. No.: 17/767,776

(22) PCT Filed: Oct. 9, 2020

(86) PCT No.: PCT/US2020/055001
§ 371 (c)(1),
(2) Date: Apr. 8, 2022

(87) PCT Pub. No.: WO2021/072204
PCT Pub. Date: Apr. 15, 2021

(65) Prior Publication Data
US 2024/0081642 A1    Mar. 14, 2024

Related U.S. Application Data

(60) Provisional application No. 62/913,863, filed on Oct. 11, 2019.

(51) Int. Cl.
*A61B 3/12*    (2006.01)
*A61B 3/00*    (2006.01)
(Continued)

(52) U.S. Cl.
CPC .......... *A61B 3/1225* (2013.01); *A61B 3/0025* (2013.01); *A61B 3/102* (2013.01);
(Continued)

(58) Field of Classification Search
CPC ..... A61B 3/1225; A61B 3/0025; A61B 3/102; G06T 7/0012; G06T 7/12;
(Continued)

(56) References Cited

U.S. PATENT DOCUMENTS 9,418,423 B2    8/2016    Wei et al.
10,366,492 B2   7/2019    Farsiu et al.
(Continued)

FOREIGN PATENT DOCUMENTS

WO    2019147871 A1    8/2019

OTHER PUBLICATIONS

Optical coherence tomography angiography (Year: 2018).*
(Continued)

*Primary Examiner* — Nizar N Sivji
(74) *Attorney, Agent, or Firm* — Talem IP Law, LLP

(57) ABSTRACT

A retinal vessel shadow view optical coherence tomography (RVSV-OCT) image can be created by receiving, at an enhanced OCT processing system, volumetric OCT scan of a patient. The system can segment the volumetric OCT scan to determine layer boundaries and delineate a boundary of interest based on the determined layer boundaries of the segmented volumetric OCT scan. En face vascular information can be extracted to create an RVSV-OCT image by determining a first offset from the boundary of interest and a second offset from the boundary of interest; extracting volumetric data from an area between the first offset and the second offset to create a three-dimensional volume; and identifying a two-dimensional surface from the three-dimensional volume, the two-dimensional surface being the
(Continued)

RVSV-OCT image. The RVSV-OCT image can be provided for analysis, for example, to evaluate retinal vascular disease in preterm infants at risk for retinopathy of prematurity.

20 Claims, 9 Drawing Sheets

(51) Int. Cl.
    *A61B 3/10*     (2006.01)
    *G06T 7/00*     (2017.01)
    *G06T 7/12*     (2017.01)

(52) U.S. Cl.
    CPC .............. *G06T 7/0012* (2013.01); *G06T 7/12* (2017.01); *G06T 2207/10101* (2013.01); *G06T 2207/20081* (2013.01); *G06T 2207/30041* (2013.01); *G06T 2207/30101* (2013.01)

(58) Field of Classification Search
    CPC . G06T 2207/10101; G06T 2207/20081; G06T 2207/30041; G06T 2207/30101; G01B 9/02083; G01B 9/02091; G06N 20/00
    See application file for complete search history.

(56) References Cited

U.S. PATENT DOCUMENTS

| | | | | |
|---|---|---|---|---|
| 11,989,877 | B2* | 5/2024 | Chauhan | G16H 70/60 |
| 2012/0127427 | A1* | 5/2012 | Guo | G06T 7/187 |
| | | | | 348/46 |
| 2014/0073917 | A1* | 3/2014 | Huang | A61B 3/0025 |
| | | | | 600/427 |
| 2014/0241605 | A1 | 8/2014 | Izatt et al. | |
| 2017/0035286 | A1* | 2/2017 | Meyer | A61B 3/1233 |
| 2017/0258321 | A1* | 9/2017 | Dastmalchi | G16H 30/20 |
| 2018/0012359 | A1 | 1/2018 | Prentasic et al. | |
| 2019/0046030 | A9 | 2/2019 | Jia et al. | |
| 2021/0133982 | A1* | 5/2021 | Bagherinia | G06V 10/761 |

OTHER PUBLICATIONS

Methods to measure blood flow and vascular reactivity in the retina (Year: 2023).*
Retinal Layer Segmentation in OCT Images With Boundary Regression and Feature Polarization (Year: 2023).*
Campbell, J. Peter, et al., "Plus Disease in Retinopathy of Prematurity: a continuous spectrum of vascular abnormality as a basis of diagnostic variability," Ophthalmology, Nov. 2016, pp. 2338-2344, vol. 123, issue 11.
Kalpathy-Cramer, Jayashree, et al., "Plus Disease in Retinopathy of Prematurity: improving diagnosis by ranking disease severity and using quantitative image analysis," Ophthalmology, Nov. 2016, pp. 2345-2351, vol. 123, issue 11.
Ouyang, Yanling, et al., "Retinal vessel diameter measurements by spectral domain optical coherence tomography," Graefe's Archive for Clinical and Experimental Ophthalmology, Apr. 2015, pp. 499-509, vol. 253, issue 4.
Rao, Rohini, et al., "Plus disease in retinopathy of prematurity: diagnostic impact of field of view," Retina, Jun. 2012, pp. 1148-1155, vol. 32, issue 6.
Tran-Viet, Du, et al., "Handheld spectral domain optical coherence tomography imaging through the undilated pupil in infants bom preterm or with hypoxic injury or hydrocephalus," Retina, Aug. 2018, pp. 1588-1594, vol. 38, issue 8.
Chiu, Stephanie J., et al., "Automatic segmentation of seven retinal layers in SDOCT images congruent with expert manual segmentation," Optics Express, Aug. 30, 2010, p. 19413, vol. 18, issue 18.
Garvin, M. K., et al., "Automated 3-D Intraretinal Layer Segmentation of Macular Spectral-Domain Optical Coherence Tomography Images," IEEE Transactions on Medical Imaging, Sep. 2009, pp. 1436-1447, vol. 28, issue 9.
Lang, Andrew, et al., "Retinal layer segmentation of macular OCT images using boundary classification," Biomedical Optics Express, Jul. 1, 2013, p. 1133, vol. 4, issue 7.
Mallipatna, Ashwin, et al., "The use of handheld spectral domain optical coherence tomography in pediatric ophthalmology practice: Our experience of 975 infants and children," Indian Journal of Ophthalmology, 2015, p. 586, vol. 63, issue 7.
International Search Report and Written Opinion Issued in International Application No. PCT/US20/55001, Mailed Date: Dec. 29, 2020, 9 Pages.
Chiang, Michael F., "Interexpert Agreement of Plus Disease Diagnosis in Retinopathy of Prematurity," Archives of Ophthalmology, Jul. 1, 2007, p. 875, vol. 125, issue 7.
Seely, Kai R., et al., "Auto-Processed Retinal Vessel Shadow View Images From Bedside Optical Coherence Tomography to Evaluate Plus Disease in Retinopathy of Prematurity," Translational Vision Science & Technology, Aug. 7, 2020, p. 16, vol. 9, issue 9.
National Eye Institute, "Retinopathy of prematurity", Jul. 10, 2019.
Early Treatment for Retinopathy of Prematurity Cooperative Group, "Revised Indications for the Treatment of Retinopathy of Prematurity: Results of the Early Treatment for Retinopathy of Prematurity Randomized Trial," Archives of Ophthalmology, Dec. 1, 2003, p. 1684, vol. 121, issue 12.
International Committee for the Classification of Retinopathy of Prematurity, "The International Classification of Retinopathy of Prematurity Revisited," Archives of Ophthalmology, Jul. 1, 2005, p. 991, vol. 123, issue 7.
The Committee for the Classification of Retinopathy of Prematurity, "An International Classification of Retinopathy of Prematurity," Archives of Ophthalmology, Aug. 1, 1984, pp. 1130-1134, vol. 102, issue 8.
Capone, Antonio, "Standard Image of Plus Disease in Retinopathy of Prematurity," Archives of Ophthalmology, Nov. 1, 2006, p. 1669, vol. 124, issue 11.
Cryotherapy for Retinopathy of Prematurity Cooperative Group, "Multicenter trial of cryotherapy for retinopathy of prematurity: preliminary results," Pediatrics, May 1988, pp. 697-706, vol. 81, issue 5.
The STOP-ROP Multicenter Study Group, "Supplemental Therapeutic Oxygen for Prethreshold Retinopathy of Prematurity (STOP-ROP), A Randomized, Controlled Trial. I: Primary Outcomes," Pediatrics, Feb. 1, 2000, pp. 295-310, vol. 105, issue 2.
Richter, Grace M., et al., "Telemedicine for Retinopathy of Prematurity Diagnosis: Evaluation and Challenges," Survey of Ophthalmology, Nov. 2009, pp. 671-685, vol. 54, issue 6.
Fierson, Walter M., et al., "Screening Examination of Premature Infants for Retinopathy of Prematurity," Pediatrics, Dec. 1, 2018, p. e20183061, vol. 142, issue 6.
Ells, Anna L., et al., "Telemedicine approach to screening for severe retinopathy of prematurity," Ophthalmology, Nov. 2003, pp. 2113-2117, vol. 110, issue 11.
Chiang, Michael F., "Accuracy and Reliability of Remote Retinopathy of Prematurity Diagnosis," Archives of Ophthalmology, Mar. 1, 2006, p. 322, vol. 124, issue 3.
Chiang, Michael F., "Telemedical Retinopathy of Prematurity Diagnosis: Accuracy, Reliability, and Image Quality," Archives of Ophthalmology, Nov. 1, 2007, p. 1531, vol. 125, issue 11.
Biten, Hilal, et al., "Diagnostic Accuracy of Ophthalmoscopy vs Telemedicine in Examinations for Retinopathy of Prematurity," JAMA Ophthalmology, May 1, 2018, p. 498, vol. 136, issue 5.
Photographic Screening for Retinopathy of Prematurity (photo-ROP) Cooperative Group, "The photographic screening for retinopathy of prematurity study (photo-ROP). Primary outcomes," Retina, Mar. 2008, pp. S47-S54, vol. 28, issue 3.
Weaver, Daniel T., et al."Telemedicine detection of type 1 ROP in a distant neonatal intensive care unit," Journal of American Association for Pediatric Ophthalmology and Strabismus, Jun. 2012, pp. 229-233, vol. 16, issue 3.
Wang, Sean K., et al., "SUNDROP: six years of screening for retinopathy of prematurity with telemedicine," Canadian Journal of Ophthalmology, Apr. 2015, pp. 101-106, vol. 50, issue 2.
Vinekar, Anand, Chaitra Jayadev, et al., "Role of tele-medicine in retinopathy of prematurity screening in rural outreach centers in

(56) References Cited

OTHER PUBLICATIONS

India—a report of 20,214 imaging sessions in the KIDROP program," Seminars in Fetal and Neonatal Medicine, Oct. 2015, pp. 335-345, vol. 20, issue 5.
Mehta, Manisha, et al., "Pilot study of the systemic effects of three different screening methods used for retinopathy of prematurity," Early Human Development, Apr. 2005, pp. 355-360, vol. 81, issue 4.
Wade, Kelly C., et al., "Safety of Retinopathy of Prematurity Examination and Imaging in Premature Infants," The Journal of Pediatrics, Nov. 2015, pp. 994-1000.e2, vol. 167, issue 5.
Szigiato, Andrei-Alexandru, et al., "Effect of Eye Masks on Neonatal Stress Following Dilated Retinal Examination: The MASK-ROP Randomized Clinical Trial," JAMA Ophthalmology, Nov. 1, 2019, p. 1265, vol. 137, issue 11.
Smith, Gillian C., et al., "Neonatal intensive care unit stress is associated with brain development in preterm infants," Annals of Neurology, Oct. 2011, pp. 541-549, vol. 70, issue 4.
Brummelte, Susanne, et al., "Procedural pain and brain development in premature newborns," Annals of Neurology, Mar. 2012, pp. 385-396, vol. 71, issue 3.
Ranger, Manon, , Ruth E. Grunau, "Early repetitive pain in preterm infants in relation to the developing brain," Pain Management, Jan. 2014, pp. 57-67, vol. 4, issue 1.
Maldonado, Ramiro S., Rachelle V. O'Connell, et al., "Dynamics of Human Foveal Development after Premature Birth," Ophthalmology, Dec. 2011, pp. 2315-2325, vol. 118, issue 12.
Vajzovic, Lejla, et al., "Maturation of the Human Fovea: Correlation of Spectral-Domain Optical Coherence Tomography Findings With Histology," American Journal of Ophthalmology, Nov. 2012, pp. 779-789.e2, vol. 154, issue 5.
Yanni, Susan E., et al., "Foveal avascular zone and foveal pit formation after preterm birth," British Journal of Ophthalmology, Jul. 2012, pp. 961-966, vol. 96, issue 7.
Vajzovic, L., et al., "Delay in Retinal Photoreceptor Development in Very Preterm Compared to Term Infants," Investigative Ophthalmology & Visual Science, Feb. 9, 2015, pp. 908-913, vol. 56, issue 2.
Lee, Helena, et al., "In Vivo Foveal Development Using Optical Coherence Tomography," Investigative Opthalmology & Visual Science, Jul. 15, 2015, p. 4537, vol. 56, issue 8.
Chavala, Sai H., et al., "Insights into Advanced Retinopathy of Prematurity Using Handheld Spectral Domain Optical Coherence Tomography Imaging," Ophthalmology, Dec. 2009, pp. 2448-2456, vol. 116, issue 12.
Lee, Annie C., et al., "Macular features from spectral-domain optical coherence tomography as an adjunct to indirect ophthalmoscopy in retinopathy of prematurity," Retina, Sep. 2011, pp. 1470-1482, vol. 31, issue 8.
Vinekar, Anand, Kavitha Avadhani, et al., "Understanding Clinically Undetected Macular Changes in Early Retinopathy of Prematurity on Spectral Domain Optical Coherence Tomography," Investigative Opthalmology & Visual Science, Jul. 15, 2011, p. 5183, vol. 52, issue 8.
Maldonado, Ramiro S., Rachelle O'Connell, et al., "Spectral-Domain Optical Coherence Tomographic Assessment of Severity of Cystoid Macular Edema in Retinopathy of Prematurity," Archives of Ophthalmology, May 1, 2012, vol. 130, issue 5.
Dubis, Adam M., et al., "Subclinical Macular Findings in Infants Screened for Retinopathy of Prematurity with Spectral-Domain Optical Coherence Tomography," Ophthalmology, Aug. 2013, pp. 1665-1671, vol. 120, issue 8.
Anwar, Samira, et al., "Potential utility of foveal morphology in preterm infants measured using hand-held optical coherence tomography in retinopathy of prematurity screening," Retina, Aug. 2020, pp. 1592-1602, vol. 40, issue 8.
Chen, Xi, et al., "Spectral-Domain OCT Findings of Retinal Vascular-Avascular Junction in Infants with Retinopathy of Prematurity," Ophthalmology Retina, Sep. 2018, pp. 963-971, vol. 2, issue 9.
Maldonado, Ramiro S., et al., "Three-Dimensional Assessment of Vascular and Perivascular Characteristics in Subjects with Retinopathy of Prematurity," Ophthalmology, Jun. 2014, pp. 1289-1296, vol. 121, issue 6.
Viehland, Christian, et al., "Ergonomic handheld OCT angiography probe optimized for pediatric and supine imaging," Biomedical Optics Express, May 1, 2019, p. 2623, vol. 10, issue 5.
Patel, Samir N., et al., "Influence of Computer-Generated Mosaic Photographs on Retinopathy of Prematurity Diagnosis and Management," JAMA Ophthalmology, Nov. 1, 2016, p. 1283, vol. 134, issue 11.
Chen, Jenny, et al., "Comparison of Autophotomontage Software Programs in Eyes with CMV Retinitis," Investigative Opthalmology & Visual Science, Dec. 9, 2011, p. 9339, vol. 52, issue 13.
Viera, Anthony J., , Joanne M. Garrett, "Understanding interobserver agreement: the kappa statistic," Family Medicine, May 2005, pp. 360-363, vol. 37, issue 5.
Shrout, Patrick E., , Joseph L. Fleiss, "Intraclass correlations: Uses in assessing rater reliability.," Psychological Bulletin, 1979, pp. 420-428, vol. 86, issue 2.
Cicchetti, Domenic V., "Guidelines, criteria, and rules of thumb for evaluating normed and standardized assessment instruments in psychology.," Psychological Assessment, Dec. 1994, pp. 284-290, vol. 6, issue 4.
Mund, Michael L., et al., "Light and Electron Microscopic Observations on the Pigmented Layers of the Developing Human Eye," American Journal of Ophthalmology, Feb. 1972, pp. 167-182, vol. 73, issue 2.
Moreno, Tomas A., et al., "Choroid Development and Feasibility of Choroidal Imaging in the Preterm and Term Infants Utilizing SD-OCT," Investigative Opthalmology & Visual Science, Jun. 14, 2013, p. 4140, vol. 54, issue 6.
Koreen, Susan, "Variation in Appearance of Severe Zone 1 Retinopathy of Prematurity During Wide-angle Contact Photography," Archives of Ophthalmology, May 27, 2008, p. 736, vol. 126, issue 5.
Gelman, Rony, et al., "Plus disease in retinopathy of prematurity: Pilot study of computer-based and expert diagnosis," Journal of American Association for Pediatric Ophthalmology and Strabismus, Dec. 2007, pp. 532-540, vol. 11, issue 6.
Wallace, David K., et al., "Agreement among pediatric ophthalmologists in diagnosing plus and pre-plus disease in retinopathy of prematurity," Journal of American Association for Pediatric Ophthalmology and Strabismus, Aug. 2008, pp. 352-356, vol. 12, issue 4.

* cited by examiner

| Relative Severity | RVSV-OCT | Clinical Grade | RVSV-OCT Grades 1 2 3 |
|---|---|---|---|
| 1 | | N | N N N |
| 2 | | N | N N N |
| 3 | | N | N N N |
| 4 | | N | N N N |
| 5 | | N | N N N |
| 6 | | N | N N N |

| Relative Severity | RVSV-OCT | Clinical Grade | RVSV-OCT Grades 1 2 3 |
|---|---|---|---|
| 7 | | PP | PP [N] PP |
| 8 | | PP | PP [U] [U] |
| 9 | | PP | PP PP PP |
| 10 | | P | [PP] [PP] [PP] |
| 11 | | P | [PP] [U] [PP] |
| 12 | | P | [PP] [PP] P |

| Relative Severity | RVSV-OCT | Clinical Grade | RVSV-OCT Grades 1 2 3 |
|---|---|---|---|
| 13 | | PP | [P] PP [P] |
| 14 | | P | P [PP] P |
| 15 | | P | P [PP] P |
| 16 | | P | P P P |
| 17 | | P | P P P |

EN FACE RETINAL VESSEL SHADOW VIEW OPTICAL COHERENCE TOMOGRAPHY IMAGES

CROSS REFERENCE TO RELATED APPLICATION(S)

This application is the U.S. National Stage Application of International Application No. PCT/US20/55001, filed Oct. 9, 2020, which claims the benefit of U.S. Provisional Application No. 62/913,863, which was filed Oct. 11, 2019, which are hereby incorporated by reference in their entirety.

GOVERNMENT RIGHTS NOTICE

This invention was made with Government support under Federal Grant nos. RO1-EY025009 awarded by the National Institutes of Health National Eye Institute, R21-EY029384 awarded by the National Institutes of Health National Eye Institute, and TL1-TR002555 awarded by the National Institutes of Health National Center for Advancing Translational Sciences. The Federal Government has certain rights to this invention.

BACKGROUND

Retinopathy of prematurity (ROP), which is characterized by disordered retinal vascularization in infants born prematurely, is the most common non-cortical cause of childhood blindness throughout the world. Longitudinal screening of at-risk infants is central to disease management, as timely identification and treatment of "treatment-warranted" ROP has been proven to decrease the risk of blindness. An important indication for treatment is the presence of "plus disease," which is defined as arterial tortuosity and venous dilation in at least two quadrants of the posterior pole, greater than that in a standardized published photograph. This is typically determined by an expert physician examining the infant at the bedside using an indirect ophthalmoscope. Because of limited numbers of expert physician examiners, a telemedicine approach has also been applied in limited settings with nurses capturing retinal color photographs and transmitting these to a reviewing physician.

BRIEF SUMMARY

Systems and methods for creating en face retinal vessel shadow view-optical coherence tomography ("RVSV-OCT") images are described. The described RVSV-OCT images can be used to evaluate retinal vascular disease, for example, in preterm infants at risk for retinopathy of prematurity (ROP).

An enhanced OCT processing system can receive a volumetric OCT scan of a patient. The system can segment the volumetric OCT scan to determine layer boundaries and delineate a boundary of interest based on the determined layer boundaries of the segmented volumetric OCT scan. En face vascular information can be extracted to create an RVSV-OCT image. The en face vascular information can be extracted to create the RVSV-OCT image by determining a first offset from the boundary of interest and a second offset from the boundary of interest; extracting volumetric data from an area between the first offset and the second offset to create a three-dimensional volume; and identifying a two-dimensional surface from the three-dimensional volume, the two-dimensional surface being the RVSV-OCT image. The RVSV-OCT image can be provided for analysis, for example, to evaluate retinal vascular disease in preterm infants at risk for retinopathy of prematurity.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The accompanying Figures and Examples are provided by way of illustration and not by way of limitation. The foregoing aspects and other features of the disclosure are explained in the following description, taken in connection with the accompanying example figures (also "FIG.") relating to one or more embodiments, in which:

FIG. 10 shows RVSV-OCT images ordered by the median (consensus) relative vascular disease severity ranking from least (1) to most (17) severe, with corresponding clinical examination grades and plus (P), pre-plus (PP), or neither (N) RVSV-OCT grades for each grader.

FIG. 11 illustrates three-grader consensus (median) relative vascular disease severity rankings for 17 RVSV-OCT montages, from least (1) to most severe (17), versus individual grader rankings.

DETAILED DESCRIPTION

Figure 1:
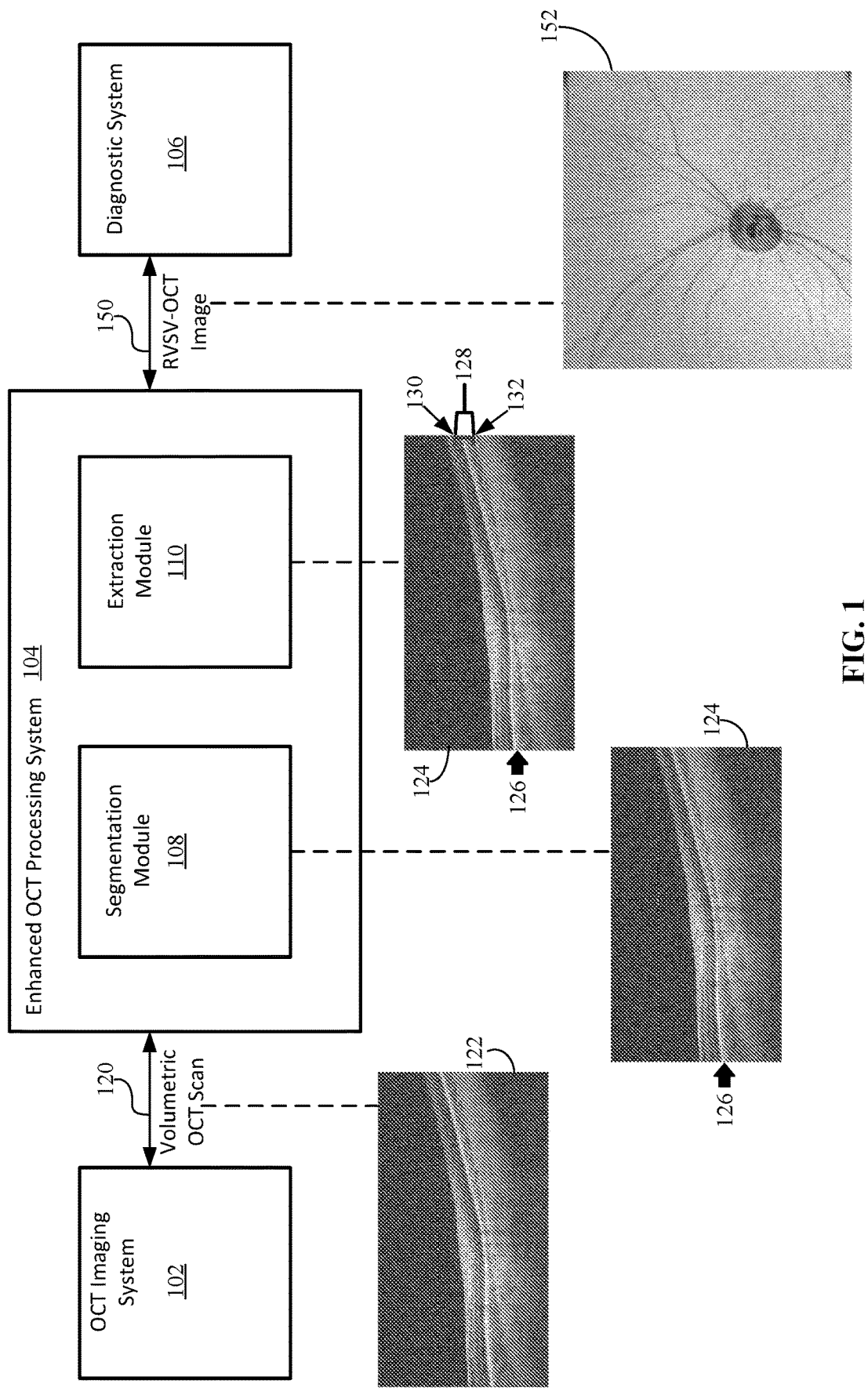
FIG. 1 illustrates an example implementation of creating en face RVSV-OCT images.

Systems and methods for creating en face retinal vessel shadow view-optical coherence tomography ("RVSV-OCT") images are described. The described RVSV-OCT images can be used to evaluate retinal vascular disease, for example, in preterm infants at risk for retinopathy of prematurity (ROP).

One drawback to current ROP screening methods is the need to shine visible light into the infant eye for the ophthalmoscopic examination or photographs. Shining visible light into the eyes produces a Bell's response (an upward rolling of the eyes) which can make viewing/imaging more difficult. The light is also stressful to infants. Preterm infant stress is known to contribute to poorer neurodevelopment. Further, color photographic images of the retina are suboptimal in infants with heavily pigmented eyes (dark brown iris and choroid), and the examination may be affected. Thus, there is an ongoing need for improved methods of detecting ROP, including plus disease.

One alternative to indirect ophthalmoscopy and fundus photography is optical coherence tomography (OCT). OCT is a non-invasive imaging modality that enables in vivo cross-sectional structural imaging of living biological tissues with micron-scale resolution. An OCT imaging system performs a volumetric scan using near-infrared light and can be used to capture cross-sectional scans of the retina with micron-scale resolution. The volumetric OCT scans can be raster scans, radial scans, or spiral scans resulting in a volume. Two-dimensional en face conventional retina view OCT images, which resemble black and white fundus photographs and can illustrate retinal vascular patterns, can be extracted from the entire OCT volume. However, the conventional OCT-generated retina view images include distracting choroidal vasculature and limited retinal vessel contrast that make analysis of the OCT-generated retina view images difficult.

The described systems and methods address several limitations of current screening modalities for the detection of plus disease and ROP. First, by leveraging OCT imaging systems, the described methods use infrared light, which is invisible and non-stressful to infants. Thus, the described methods advantageously overcome the problem of stress associated with imaging with visible light. Stress can be further reduced through the use of a non-contact OCT imaging system. In addition, infrared light imaging at the level of the retinal pigment epithelium is independent of the pigmentation of the choroid (which can vary by race and with disease) and is based on the contrast of the shadowing from hemoglobin in the retinal vessels against retinal tissue reflectivity. Thus, second, the methods are advantageously not limited in infants with dark pigmentation. Third, the described methods involve segmentation of retinal layers. The segmentation of retinal layers allows for the elimination of choroid vasculature, which can obscure the desired image information. Indeed, the described segmentation increases retinal vessel contrast and visibility and removes confounding choroidal vascular patterns that can be problematic for human grading or automated vessel analysis programs. This benefit is achieved by extracting the RVSV-OCT images exclusively from volumetric data around the segmented layer.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. The methods and compositions disclosed herein can be used on a sample either in vitro (for example, on isolated cells or tissues) or in vivo in a subject (i.e. living organism, such as a patient). In some embodiments, the subject comprises a human who is undergoing ROP screening with the method described herein.

Unless otherwise defined, all technical terms used herein have the same meaning as commonly understood by one of ordinary skill in the art to which this disclosure belongs.

FIG. 1 illustrates an example implementation of creating en face RVSV-OCT images. Referring to FIG. 1, there can be communication between an OCT imaging system 102, an enhanced OCT processing system 104, and a diagnostic system 106. The enhanced OCT processing system 104 can include or communicate with a segmentation module 108 and an extraction module 110. In some cases, the enhanced OCT processing system 104 includes or communicates with one or more data resources (not shown).

The OCT imaging system 102 can be used to scan the eyes of a patient for the purpose of detecting vascular changes. The OCT imaging system 102 may be any suitable OCT imaging system, including commercial OCT imaging systems. The OCT imaging system can be, for example, a hand-held OCT imaging system or a tabletop OCT imaging system. The tabletop OCT imaging system can be used to image an infant held upright using a flying-baby pose.

The enhanced OCT processing system 104 can receive (120) a volumetric OCT scan from the OCT imaging system 102. The OCT imaging system 102 uses near-infrared light to capture a series of depth-resolved, cross-sectional, two-dimensional images (i.e., B-scans) of the retina with micron-scale resolution. Taken as a whole, this series of cross-sectional images results in a three-dimensional volumetric OCT scan. Cross-section 122 shows an example of a single cross-section (i.e., B-scan) of the volumetric OCT scan received (120) from the OCT imaging system 102. Volumetric OCT scans can be generated based on different scan patterns, where individual cross-sectional OCT images are captured at varying positions or angles that result in a volume (e.g. raster scans, radial scans, or spiral scans). In some cases, the volumetric OCT scan is comprised of high-density OCT images. In some cases, the volumetric OCT scan is comprised of standard-quality OCT images from commercially available OCT imaging systems.

The segmentation module 108 of the enhanced OCT processing system 104 can segment the volumetric OCT scan to determine layer boundaries. A layer boundary is a separation of two regions on an image. Any layer segmentation process that identifies layer boundaries can be used to segment the volumetric OCT scan. In some cases, the layer boundaries are retinal layer boundaries. In some cases, the layer boundaries are choroid layer boundaries. In some cases, the layer boundaries delineate pathologies.

Once the volumetric OCT scan is segmented and the layer boundaries are determined, a boundary of interest can be delineated based on those determined layer boundaries. The boundary of interest can be any one of the determined layer boundaries. For example, the boundary of interest can be Bruch's membrane (BM) or another approximate marker such as an adjacent retinal pigment epithelium (RPE) (e.g. top margin, center).

The boundary of interest can be used to isolate certain vasculature. For example, a specific region determined by a layer boundary may contain vessels of interest. That specific layer boundary can be delineated as the boundary of interest to isolate those vessels of interest.

The boundary of interest can be used to isolate certain pathologies. For example, a specific region determined by a layer boundary may contain a pathology of interest. That specific layer boundary can be delineated as the boundary of interest to isolate the pathology of interest.

Segmented cross-section 124 shows the cross-section 122 after the segmentation and delineation process performed by the segmentation module 108. In the illustrative example, the boundary of interest is Bruch's membrane. Arrow 126 shows the delineation of Bruch's membrane location across the segmented cross-section 124.

The extraction module 110 of the enhanced OCT processing system 104 can extract enface vascular information from the segmented volumetric OCT scan to create an RVSV-OCT image. The extraction module 110 can perform the extraction by determining a first offset from the boundary of interest and a second offset from the boundary of interest.

In some cases, the offsets (e.g., the first offset and/or the second offset) are constant offsets. In some cases, the offsets (e.g., the first offset and/or the second offset) are non-constant offsets. The offsets may be 0 (e.g., at the boundary of interest), above the boundary of interest, or below the boundary of interest.

In an example where the boundary of interest is Bruch's membrane or another approximate marker such as the adjacent RPE (e.g. top margin, center), the first offset could be a location above the boundary of interest and the second offset could be a location below the boundary of interest. The location above the boundary of interest and the location below the boundary of interest can be determined based on a number of microns above the boundary of interest and the number of microns below the boundary of interest that maximizes visualization of the retinal vasculature.

In the illustrative example, segmented cross-section 124 shows a first offset 130 at a location above the boundary of interest the area (shown by arrow 126) and a second offset 132 at a location below the boundary of interest.

The extraction module 110 can extract volumetric data from an area between the first offset and the second offset to create a three-dimensional volume. The three-dimensional volume provides a restricted volume from which an RVSV-OCT image can be extracted.

In the illustrative example, volumetric data can be extracted from the area 128 between the first offset 130 and the second offset 132. Here, the area 128 is centered around the boundary of interest, and the extraction may be a selective extraction of OCT imaging voxels from the area 128 centered around the Bruch's membrane location (e.g., arrow 126).

The area centered around the boundary of interest provides a narrow axial window bracketed around the Bruch's membrane or RPE for the purpose of enhancing the view of the retinal vessel shadows and removing choroidal patterns.

The extraction module 110 can identify a two-dimensional surface from the three-dimensional volume. The two-dimensional surface is the RVSV-OCT image. The two-dimensional surface can be identified from the three-dimensional volume a variety of ways. In some cases, the extraction module can calculate a mean pixel intensity of the three-dimensional volume to identify the two-dimensional surface. The mean pixel intensity can identify contrasting colors from the depth of the three-dimensional volume. The result of the mean pixel intensity is a single pixel that can be represented en face. Thus, the RVSV-OCT image is extracted from this mean pixel intensity.

In some cases, the extraction module can calculate a maximum pixel intensity of the three-dimensional volume to identify the two-dimensional surface. In some cases, the extraction module can calculate an average maximum pixel intensity of the three-dimensional volume to identify the two-dimensional surface.

Advantageously, the extraction module 110 can use set regions of deep retinal segmentation around the level of the boundary of interest to augment the contrast and appearance of the retinal vessels in an en face view.

The enhanced OCT processing system 104 can provide (150) the RVSV-OCT image to the diagnostic system 106 for analysis. RVSV-OCT image 152 shows an example of an RVSV-OCT image created from the volumetric OCT scan received from the OCT imaging system 102.

In some cases, the RVSV-OCT image can be provided to the diagnostic system 106 by communicating the image files over a network. For example, the diagnostic system 106 may be located at a remote device and the receipt of the RVSV-OCT image is received over the network. In some cases, the diagnostic system 106 may be located at the OCT imaging system 102. In this case, the RVSV-OCT image may be provided to the diagnostic system 106 where the image is output to a display coupled to the OCT imaging system 102.

In some cases, multiple volumetric OCT scans of the same eye can be captured by the OCT imaging system 102 (e.g., at varying positions or angles) and processed by the enhanced OCT processing system 104 to generate a series of RVSV-OCT images. These individual RVSV-OCT images can be combined to generate an enhanced RVSV-OCT image that is provided to the diagnostic system 106. For example, the individual RVSV-OCT images can be montaged using retinal montage software to produce a wider field of view RVSV-OCT image.

RVSV-OCT images, including enhanced RVSV-OCT images, can be used to analyze or extract data in multiple ways. Advantageously, RVSV-OCT images can be treated similarly to color photographs for evaluation of plus disease in ROP, where they are graded by expert reviewers. RVSV-OCT images can also be analyzed using any of the wide range of tools used to analyze other photographs (e.g., color, red-free, green, scanning laser ophthalmoscopic images). The analysis of RVSV-OCT images can be used to determine, for example, severity of ROP, dilation and tortuosity of retinal vessels in infant eyes with ROP, severity of retinal vascular disease or of pre-plus and plus disease (e.g., ROP-tool, or artificial intelligence or deep learning methods to grade vascular patterns, branching, tortuosity).

In one example, the diagnostic system 106 is a clinician device. In this example, the RVSV-OCT image can be provided for human review of the images "as is." The RVSV-OCT image can be displayed to the clinician and then analyzed. The analysis can include expert grading by physicians (e.g., clinician grading), graders or groups of non-experts. This analysis can be comparable to methods used to view color or black and white photographs.

In another example, the diagnostic system 106 is an image processing system. In this example, the RVSV-OCT image can be provided for conventional image processing or AI machine learning image processing techniques (categorization) to extract parameters of vessels (e.g. dilation and tortuosity) or of optic nerve head (area).

In yet another example, the diagnostic system 106 can provide computer-based image analysis (with or without human input). For example, a semiautomated computer program, such as ROPtool, can be used to extract vessels, where a human designates vessels and the semiautomated computer program traces out and analyzes the designated vessels.

In yet another example, the diagnostic system 106 can provide any other image processing, machine learning, or AI methods to extract the vessel data (and or optic nerve data)—e.g. classic binarize/skeletonize or variations on this that make use of the characteristics of OCT data. For example, the RVSV-OCT image can be provided to an artificial intelligence (AI) system where the AI system evaluates the RVSV-OCT image and automatically outputs a diagnostic.

In some cases, the diagnostic system 106 stores the results of each analysis of the RVSV-OCT image in order to create a chart that tracks changes over time for a patient.

Figure 5:
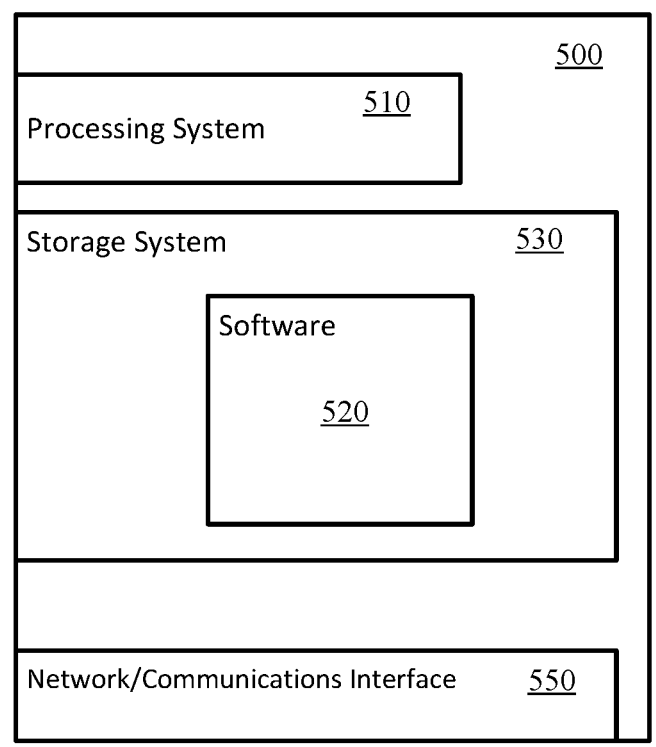
FIG. 5 illustrates components of an example computing system that may be used to implement certain methods and services described herein.

The segmentation module 108 and the extraction module 110 may be implemented as software or hardware (or a combination thereof) on a server (e.g., an enhanced OCT processing server), which may be an instantiation of system 500 as described in FIG. 5. In some cases, some or all of the features carried out by the segmentation module 108 and the extraction module 110 are carried out at the OCT imaging system 102.

In some cases, the segmentation module 108 and the extraction module 110 may be part of separate systems. For example, some or all of the features carried out by the segmentation module 108 may be carried out at the OCT imaging system 102 and some or all of the features carried out by the extraction module 110 may be carried out at the enhanced OCT processing system 104.

Components (computing systems, storage resources, and the like of the OCT imaging system 102, enhanced OCT processing system 104, and diagnostic system 106) in the example implementation may operate on or in communication with each other over a network (not shown). The network can be, but is not limited to, a cellular network (e.g., wireless phone), a point-to-point dial up connection, a satellite network, the Internet, a local area network (LAN), a wide area network (WAN), a WiFi network, an ad hoc network or a combination thereof such networks are widely used to connect various types of network elements, such as hubs, bridges, routers, switches, servers, and gateways. The network may include one or more connected networks (e.g., a multi-network environment) including public networks, such as the Internet, and/or private networks such as a secure enterprise private network. Access to the network may be provided via one or more wired or wireless access networks as will be understood by those skilled in the art.

As will also be appreciated by those skilled in the art, communication networks can take several different forms and can use several different communication protocols. Certain embodiments of the invention can be practiced in distributed-computing environments where tasks are performed by remote-processing devices that are linked through a network. In a distributed-computing environment, program modules can be located in both local and remote computer-readable storage media.

Communication to and from the components may be carried out, in some cases, via application programming interfaces (APIs). An API is an interface implemented by a program code component or hardware component (hereinafter "API-implementing component") that allows a different program code component or hardware component (hereinafter "API-calling component") to access and use one or more functions, methods, procedures, data structures, classes, and/or other services provided by the API-implementing component. An API can define one or more parameters that are passed between the API-calling component and the API-implementing component. The API is generally a set of programming instructions and standards for enabling two or more applications to communicate with each other and is commonly implemented over the Internet as a set of Hypertext Transfer Protocol (HTTP) request messages and a specified format or structure for response messages according to a REST (Representational state transfer) or SOAP (Simple Object Access Protocol) architecture.

Figure 2A:
FIGS. 2A and 2B show examples for comparisons of a conventional OCT-generated retina view image and an RVSV-OCT image.
Figure 2B:
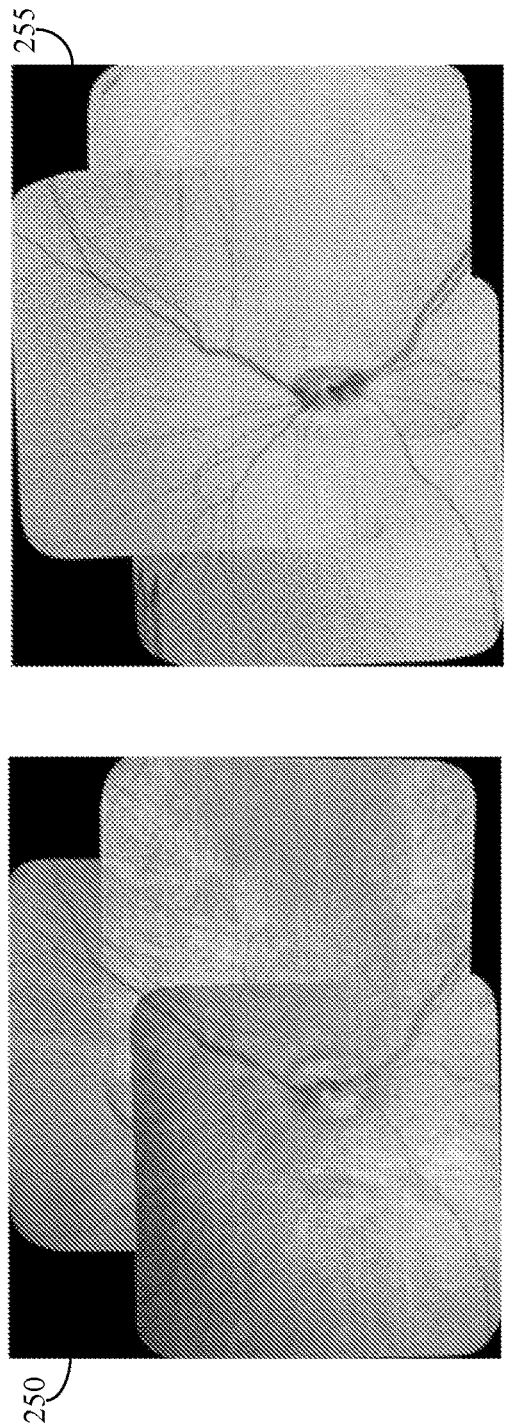

FIGS. 2A and 2B show examples for comparison between a conventional OCT-generated retina view image montage and an RVSV-OCT image montage. OCT-generated conventional retina view images can be extracted from volumetric OCT scans using mean pixel intensity of data from the entire cross-sectional scan. RVSV-OCT images can be extracted from volumetric data brackets of an area between a first offset and a second offset from the boundary of interest as described in FIG. 1. The example RVSV-OCT images can be created using processes 300 and 320 as described with respect to FIGS. 3A and 3B, respectively.

Referring to FIGS. 2A and 2B, examples of conventional OCT-generated retina view images include OCT-generated retina view image montage 205 and OCT-generated retina view image montage 250. Examples of RVSV-OCT images include RVSV-OCT image montage 210 and RVSV-OCT image montage 255.

As can be seen, the conventional OCT-generated retina view images include distracting choroidal vasculature that make analysis of the OCT-generated retina view images difficult. For example, due to the poor visibility and distinctness of retinal vessels, differentiating retinal vessels in conventional OCT-generated retina view images becomes difficult.

The RVSV-OCT images have several advantages over the conventional OCT-generated retina view images. The RVSV-OCT images exclude confounding imaging data and are useful for evaluation of retinal disease severity, such as ROP. Indeed, the extraction of RVSV-OCT images exclusively from volumetric data from an area between a first offset and a second offset from the boundary of interest results in the elimination of distracting choroidal vasculature. The elimination of choroidal patterns can improve visualization of retinal vessels, and is advantageous for grading by clinicians or analysis by semi-automated or machine learning-based software.

Figure 3A:
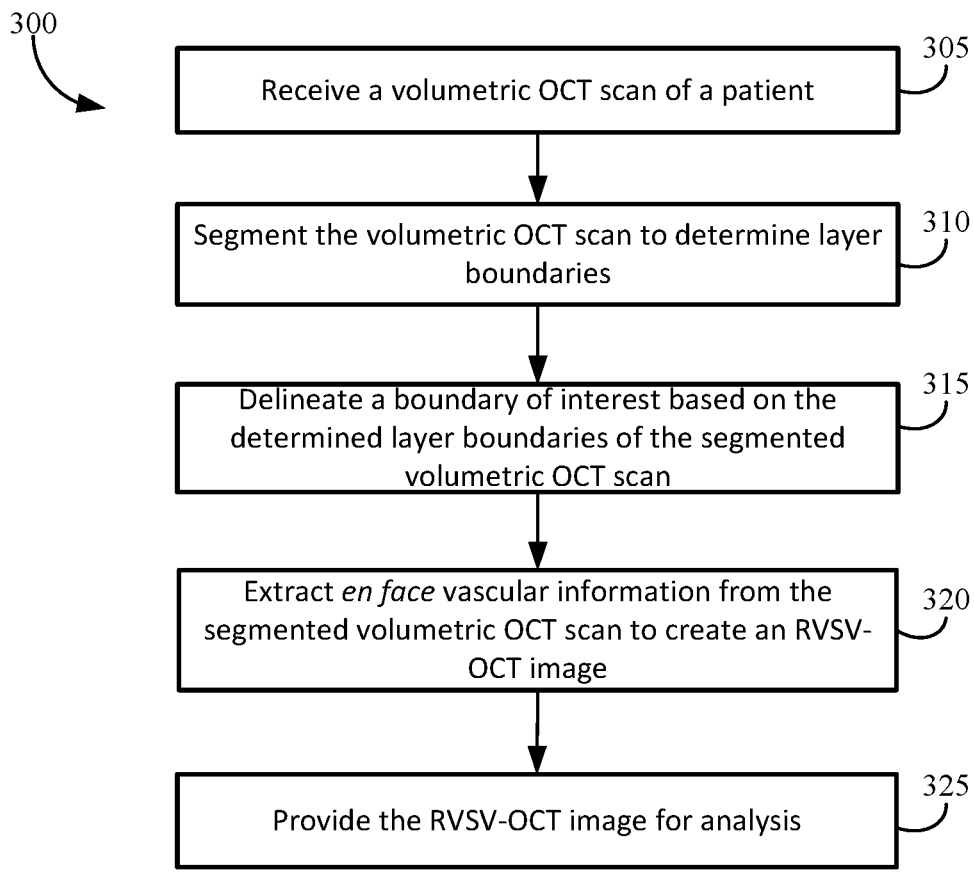
FIG. 3A illustrates a process flow diagram for creating an enface RVSV-OCT image according to an embodiment of the invention.
Figure 3B:
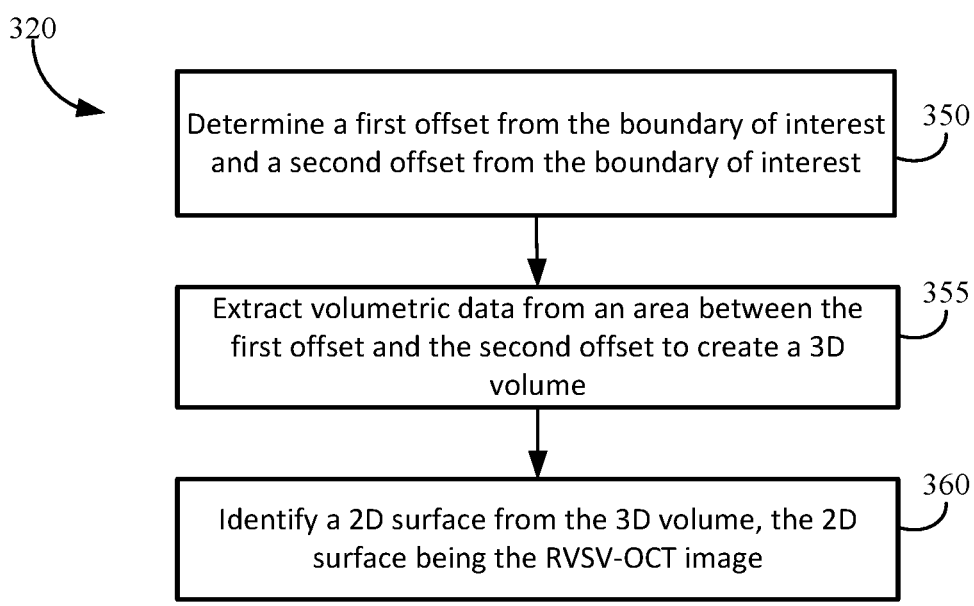
FIG. 3B illustrates a process flow diagram for extracting en face vascular information from a segmented volumetric scan to create an RVSV-OCT image according to an embodiment of the invention.

FIG. 3A illustrates a process flow diagram for creating an en face RVSV-OCT image according to an embodiment of the invention; and FIG. 3B illustrates a process flow diagram for extracting en face vascular information from a segmented volumetric scan to create an RVSV-OCT image according to an embodiment of the invention. An enhanced OCT processing system performing process 300 described with respect to FIG. 3A and process 320 described with respect to FIG. 3B can be implemented by an enhanced OCT processing server, which can be embodied with respect to computing system 500 as shown in FIG. 5.

Referring to process 300 of FIG. 3A, the enhanced OCT processing system can receive (305) a volumetric OCT scan of a patient. OCT uses near-infrared light to capture cross-sectional scans of the retina with micron-scale resolution. Indeed, the volumetric OCT scan provides micron resolution three-dimensional data of the retinal layers. The volumetric OCT scan can include raster scans, radial scans, or spiral scans resulting in a volume. In some cases, the volumetric OCT scan is comprised of high-density OCT images. In some cases, the volumetric OCT scan is comprised of standard-quality OCT images from commercially available OCT imaging systems.

The volumetric OCT scan can be received from an OCT imaging system directly or can be received from a storage containing images obtained from an OCT imaging system. In some cases, the volumetric OCT scan may be a bedside OCT capture of OCT volume. The OCT imaging system can be, for example, a hand-held OCT imaging system or a tabletop OCT imaging system. The tabletop OCT imaging system can be used to image an infant held upright using a flying-baby pose.

The patient from which the volumetric OCT scan is taken may be an adult, a child, or an infant. For example, in the case where the volumetric OCT scan is from an infant, the OCT imaging system can be used to scan the eyes of premature infants for the purpose of detecting vascular changes. One type of optical imaging device suitable for performing scanning of the patient is a hand-held swept-source optical coherence tomography (SS-OCT) described in PCT/US2019/015036. The light source for scanning illumination is provided in the infrared range. By using infrared light, the infant is not bothered by visible light, is less stressed, and is less likely to have a Bell's response.

The SS-OCT system captures multiple A-scans of the retina (which can be thought of as pixels of top-down imaging) and a reconstruction from raster scans results in retinal volumes. These scans are useful for the examination of cross-sectional retinal structures and for tracing out retinal vascular patterns to create a three-dimensional map. Those manual tracings require many person-hours per image and are not feasible for clinical care, point of care reporting, or telemedicine. The speed of capture and density of pixels is useful for the extraction of meaningful vascular patterns and the lack of motion artifact. Motion artifact can limit the utility of the vascular images.

A segmentation module, such as segmentation module 108 as described with respect to FIG. 1, of the enhanced OCT processing system can segment (310) the volumetric OCT scan to determine layer boundaries and delineate (315) a boundary of interest based on the determined layer boundaries of the segmented volumetric OCT scan. Any layer segmentation process that identifies layer boundaries can be used to segment the volumetric OCT scan. For example, the segmentation can be done manually or could be performed by AI learning from the segmented data. In some cases, the layer boundaries are retinal layer boundaries. In some cases, the layer boundaries are choroid layer boundaries.

As previously described, the boundary of interest can be any one of the determined layer boundaries. For example, the boundary of interest can be Bruch's membrane (BM) or another approximate marker such as an adjacent retinal pigment epithelium (RPE) (e.g. top margin, center). The boundary of interest can be used to isolate certain vasculature. For example, a specific layer boundary may contain vessels of interest. That specific layer boundary can be delineated as the boundary of interest to isolate those vessels of interest.

The segmentation (310) and delineation (315) steps of process 300 can be based on the age of the patient. The anatomy of an infant's eye is different than the anatomy of an adult's eye. For example, an infant has a different number of layers than a fully developed adult. Further, the choroid is more visible in an infant than an adult. Thus, using the same parameters for an adult and an infant can cause problems with the results of segmenting the volumetric OCT scan. In some cases, a mapping between age and eye anatomy may be maintained in one or more storage resources in which the enhanced OCT processing system includes or communicates with.

Advantageously, infant specific changes in the developing inner layers (thinning and coalescing) and outer layers (forming/appearing and thickening) are addressed using a separate segmentation algorithm for an infant. That is, segmentation for an infant uses specific knowledge of unique layer characteristics of the preterm infant eye to enable reproducible segmentation without notable need for human correction.

Figures 4A, 4B:
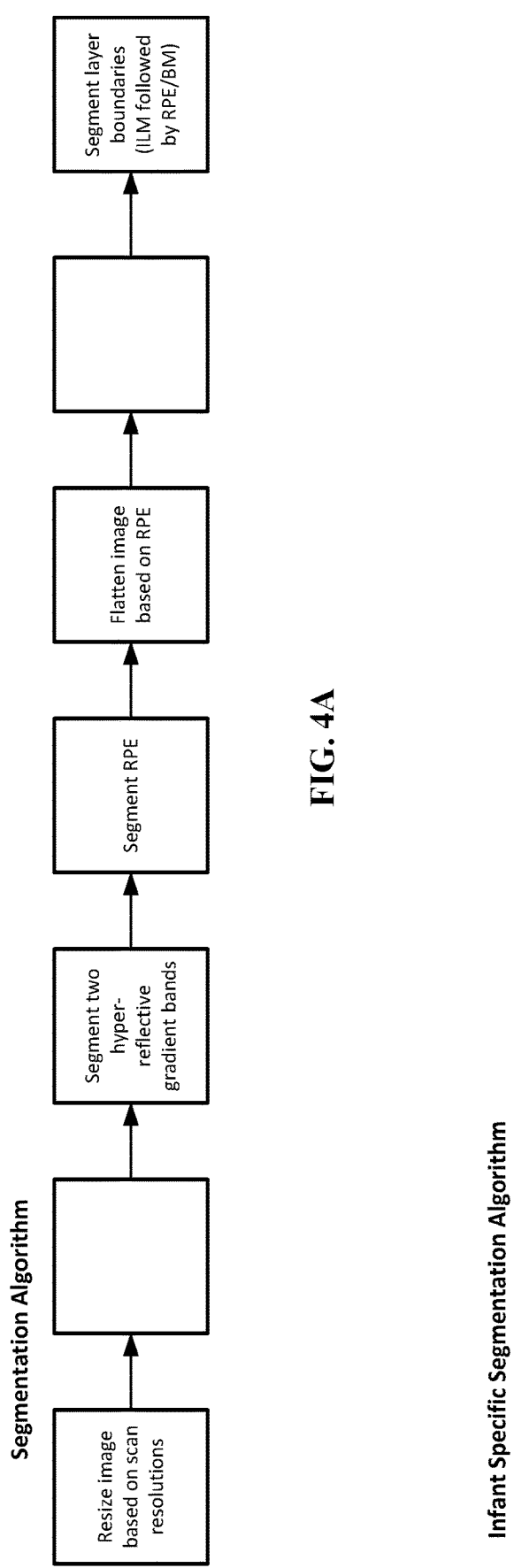
FIG. 4A illustrates an example conventional segmentation algorithm.
FIG. 4B illustrates an example infant specific segmentation algorithm.

FIG. 4A illustrates an example conventional segmentation algorithm; and FIG. 4B illustrates an example infant specific segmentation algorithm. In some cases, prior to performing the segmentation, the volumetric OCT scan is converted to an image or readable format, such as tiff file type. Referring to FIG. 4A, in the example conventional segmentation algorithm, the image can be resized based on the volumetric OCT scan resolution. Then, two hyper-reflective gradient bands are segmented. The RPE is segmented and the image is flattened based on the RPE. The layer boundaries are then segmented (ILM followed by RPE/BM).

In some cases, an infant specific, automatic OCT segmentation method is used to segment and delineate the layer boundaries. As an example, the infant specific, automatic OCT segmentation method can enable robust auto-segmentation of the infant retina into layers. This type of segmentation has typically been used to compare thicknesses of different layers or the three-dimensional volume, as the layers develop or are affected by disease. The segmentation that takes into account the unique layers of the infant eye allows extraction of enface visualization of the signal from the inner retinal vasculature in infants, a technique that is standard in OCT-angiography in adults.

Referring to FIG. 4B, in the example infant specific segmentation algorithm the volumetric OCT scan is converted to an image or readable format, such as tiff file type. The image can be resized based on the volumetric OCT scan resolutions and age using a scan length conversion factor. The retina is isolated using thresholding (images have artifacts above/below). Then, three hyper-reflective gradient bands are segmented to account for the choroid. The RPE is segmented and the image is flattened based on the RPE. Since the images are taller than they are wide, the image is cropped. The layer boundaries are then segmented (ILM followed by RPE/BM).

An example of a segmentation algorithm, including both adult and pediatric segmentation can be found in U.S. Pat. No. 10,366,492 B2.

Returning to FIG. 3A, an extraction module, such as extraction module 110 as described with respect to FIG. 1, of the enhanced OCT processing system can extract (320) en face vascular information from the segmented volumetric OCT scan to create an RVSV-OCT image.

In one example, the extraction of the vascular information removes choroidal pattern below and the "variable retinal pattern" above the boundary of interest, and results in high contrast vessels against a fairly constant "background" of a different contrast. That is, the extraction process can pull out retinal vessels by using their extracted shadows. The isolation of the choroidal layers from the retinal layers allows separate analysis from that of the retina.

The extraction of the vascular information provides additional information, such as thickness maps and three-dimensional information (from the full thickness of the retina or other selective layers). This three-dimensional thickness data can be used to augment the two-dimensional en face view. Further, the extraction of the vascular information creates additional patient information of value, such as a view of the optic nerve head size at the level of the Bruch's membrane opening.

The extraction of en face vascular information from the segmented volumetric OCT scan to create the RVSV-OCT image can be performed according to process 320 shown in FIG. 3B. Referring to FIG. 3B, in process 320, the extraction module can determine (350) a first offset from the boundary of interest and a second offset from the boundary of interest.

As previously described, in some cases, the offsets (e.g., the first offset and/or the second offset) are constant offsets. In some cases, the offsets are non-constant offsets. The offsets may be 0 (e.g., at the boundary of interest), above the boundary of interest, or below the boundary of interest.

In an example where the boundary of interest is Bruch's membrane or another approximate marker such as the adjacent RPE (e.g. top margin, center), the first offset could be a location above the boundary of interest and the second offset could be a location below the boundary of interest. The location above the boundary of interest and the location below the boundary of interest can be determined based on a number of microns above the boundary of interest and the number of microns below the boundary of interest that maximizes visualization of the retinal vasculature.

The number of microns can be dependent on age of the patient. In an example where the patient is an infant, the location above the boundary of interest is a location 20 microns above the boundary of interest and the location below the boundary of interest is a location 20 microns below the boundary of interest. In an example where the patient is an adult, the location above the boundary of interest is a location 10 microns above the boundary of interest and the location below the boundary of interest is a location 10 microns below the boundary of interest.

The extraction module can extract (355) volumetric data from an area between the first offset and the second offset to create a three-dimensional volume. The three-dimensional volume provides a restricted volume in which the RVSV-OCT image can be extracted. As an example, the extraction may be a selective extraction of OCT imaging voxels from the area between the first offset and the second offset.

In one example where the first offset is zero (e.g., at the boundary of interest) and the second offset is below the boundary of interest, the volumetric data is extracted from an area between the location of the first offset (the boundary of interest) and the location of the second offset below the boundary of interest.

In another example where the first offset is above the boundary of interest and the second offset is zero (at the boundary of interest), the volumetric data is extracted from an area between the location of the first offset above the boundary of interest and the location of the second offset (at the boundary of interest).

The extraction module can identify (360) a two-dimensional surface from the three-dimensional volume. The two-dimensional surface is the RVSV-OCT image. The two-dimensional surface can be identified from the three-dimensional volume a variety of ways. In some cases, the extraction module can calculate a mean pixel intensity of the three-dimensional volume to identify the two-dimensional surface. The mean pixel intensity can identify contrasting colors from the depth of the three-dimensional volume. The result of the mean pixel intensity is a single pixel that can be represented en face. Thus, the RVSV-OCT image is extracted from this mean pixel intensity.

In some cases, the extraction module can calculate a maximum pixel intensity of the three-dimensional volume to identify the two-dimensional surface. In some cases, the extraction module can calculate an average maximum pixel intensity of the three-dimensional volume to identify the two-dimensional surface.

Returning to FIG. 3A, the enhanced OCT processing system can provide (325) the RVSV-OCT image for analysis. The RVSV-OCT image can be provided to a diagnostic system, such as diagnostic system 106 as described with respect to FIG. 1, for analysis. The diagnostic system can be implemented by a system embodied as described with respect to system 500 shown in FIG. 5.

The resulting RVSV-OCT image and optic nerve opening view, all from the OCT volume, can be used to analyze or extract data in multiple ways. Advantageously, through the diagnostic system, RVSV-OCT images can be treated similarly to color photographs for evaluation of plus disease in ROP, where they are graded by expert reviewers. The RVSV-OCT images can be montaged using retinal montage software to produce a wider field of view image. The RVSV-OCT images can also be analyzed using any of the wide range of tools used to analyze other photographs (e.g., color, red-free, green, scanning laser ophthalmoscopic images). The analysis of RVSV-OCT images can be used to determine, for example, severity of ROP, dilation and tortuosity of retinal vessels in infant eyes with ROP, severity of retinal vascular disease or of pre-plus and plus disease (e.g., ROPtool, or artificial intelligence or deep learning methods to grade vascular patterns, branching, tortuosity).

In one example, the RVSV-OCT image can be provided to a clinician device for human review of the images "as is." The analysis can include expert grading by physicians (e.g., clinician grading), graders or groups of non-experts. This analysis can be comparable to methods used to view color or black and white photographs.

In another example, the RVSV-OCT image can be provided to an image processing system for conventional image processing or AI machine learning image processing techniques (categorization) to extract parameters of vessels (e.g. dilation and tortuosity) or of optic nerve head (area).

In yet another example, the RVSV-OCT image can be provided for computer-based image analysis (with or without human input). For example, an ROPtool can be used to extract vessels, where a human designates vessels and the ROPtool traces out and analyzes the designated vessels.

In yet another example, the RVSV-OCT image may be provided for any other image processing, machine learning, or AI methods to extract the vessel data and/or optic nerve data (e.g., classic binarize/skeletonize or variations on this that make use of the characteristics of OCT data).

In yet another example, the RVSV-OCT image may be provided to a semi- or fully automatic plus disease classification system (e.g., machine learning) for analysis.

FIG. 5 illustrates components of an example computing system that may be used to implement certain methods and services described herein. Referring to FIG. 5, system 500 may be implemented within a single computing device or distributed across multiple computing devices or sub-systems that cooperate in executing program instructions. The system 500 can include one or more blade server devices, standalone server devices, personal computers, routers, hubs, switches, bridges, firewall devices, intrusion detection devices, mainframe computers, network-attached storage devices, and other types of computing devices. The system hardware can be configured according to any suitable computer architectures such as a Symmetric Multi-Processing (SMP) architecture or a Non-Uniform Memory Access (NUMA) architecture.

The system 500 can include a processing system 510, which may include one or more processors and/or other circuitry that retrieves and executes software 520 from storage system 530. Processing system 510 may be implemented within a single processing device but may also be distributed across multiple processing devices or sub-systems that cooperate in executing program instructions.

Storage system(s) 530 can include any computer readable storage media readable by processing system 510 and capable of storing software 520. Storage system 530 may be implemented as a single storage device but may also be implemented across multiple storage devices or sub-systems co-located or distributed relative to each other. Storage system 530 may include additional elements, such as a controller, capable of communicating with processing system 510. Storage system 530 may also include storage devices and/or sub-systems on which data is stored. System 500 may access one or more storage resources in order to access information to carry out any of the processes indicated by software 520.

Software 520, including routines for performing processes, such as process 300 and process 320 for an enhanced OCT processing system, may be implemented in program instructions and among other functions may, when executed by system 500 in general or processing system 510 in particular, direct the system 500 or processing system 510 to operate as described herein.

System 500 may represent any computing system on which software 520 may be staged and from where software 520 may be distributed, transported, downloaded, or otherwise provided to yet another computing system for deployment and execution, or yet additional distribution.

In embodiments where the system 500 includes multiple computing devices, the server can include one or more communications networks that facilitate communication among the computing devices. For example, the one or more communications networks can include a local or wide area network that facilitates communication among the computing devices. One or more direct communication links can be included between the computing devices. In addition, in some cases, the computing devices can be installed at geographically distributed locations. In other cases, the multiple computing devices can be installed at a single geographic location, such as a server farm or an office.

A network/communications interface 550 may be included, providing communication connections and devices that allow for communication between system 500 and other computing systems (not shown) over a communication network or collection of networks (not shown) or the air.

In some embodiments, system 500 may host one or more virtual machines.

Certain techniques set forth herein with respect to the application and/or sensitivity feature service may be described in the general context of computer-executable instructions, such as program modules, executed by one or more computing devices. Generally, program modules include routines, programs, objects, components, and data structures that perform particular tasks or implement particular abstract data types.

Alternatively, or in addition, the functionality, methods and processes described herein can be implemented, at least in part, by one or more hardware modules (or logic components). For example, the hardware modules can include, but are not limited to, application-specific integrated circuit (ASIC) chips, field programmable gate arrays (FPGAs), system-on-a-chip (SoC) systems, complex programmable logic devices (CPLDs) and other programmable logic devices now known or later developed. When the hardware modules are activated, the hardware modules perform the functionality, methods and processes included within the hardware modules.

Certain embodiments may be implemented as a computer process, a computing system, or as an article of manufacture, such as a computer program product or computer-readable storage medium. Certain methods and processes described herein can be embodied as software, code and/or data, which may be stored on one or more storage media. Certain embodiments of the invention contemplate the use of a machine in the form of a computer system within which a set of instructions, when executed by hardware of the computer system (e.g., a processor or processing system), can cause the system to perform any one or more of the methodologies discussed above. Certain computer program products may be one or more computer-readable storage media readable by a computer system (and executable by a processing system) and encoding a computer program of instructions for executing a computer process. It should be understood that as used herein, in no case do the terms "storage media", "computer-readable storage media" or "computer-readable storage medium" consist of transitory carrier waves or propagating signals.

Example Implementation and Results

The described method can create an en face RVSV-OCT image, optimized for visualization of the retinal vasculature, from investigational, high-speed, noncontact, swept source (SS)-OCT captured at the bedside in awake infants. The feasibility of using montaged RVSV-OCT images for grading posterior pole ROP vascular disease severity by ophthalmologists was evaluated, as well as if there are differences in RVSV-OCT vessel visualization based on fundus pigmentation.

The exploratory study was performed as part of the analysis of retinal vasculature in ROP for BabySTEPS (an institutional review board-approved prospective, observational study registered with clinicaltrials.gov [registration: NCT02887157]). The study was approved by the Duke University Health System institutional review board, is compliant with the Health Insurance Portability and Accountability Act of 1996, and is adherent to all tenets of the Declaration of Helsinki. Between September 2016 and November 2019, 118 preterm infants were enrolled in BabySTEPS, 102 of which underwent research bedside, noncontact, handheld SS-OCT imaging of both eyes performed on the same day as clinical ROP screening examinations. Prior to enrollment, informed consent was obtained from a parent or legal guardian after explanation of the nature and possible consequences of the study.

Bedside SS-OCT imaging with an investigational system featuring a 200 kHz, 1060 nm SS laser (Axsun Technologies Inc., Billerica, MA) and a 700 g handheld, noncontact probe was performed. Anisotropic 10×10 mm OCT volumes with 950 A-scans per B-scan and 256 B-scans per volume were captured. Two B-scans were acquired at each lateral location on the slow axis to allow for averaging in post-processing. The primary imaging goal was to capture the fovea, optic nerve, and papillomacular bundle for each eye; a secondary goal was to capture a portion of the temporal peripheral retina. During standard-of-care clinical ROP examinations, fellowship-trained pediatric ophthalmologists (SFF and SGP) recorded fundus pigmentation (blond, medium, or dark) and ROP posterior pole vascular severity (plus, pre-plus, or neither) on a standard template. The participants' medical records were reviewed for these clinical examination findings, as well as demographic and general health information.

As part of the primary BabySTEPS study goal to "determine severity of ROP by analysis of OCT" (clini-caltrials.gov registration: NCT02887157), numerous methods to extract vascular information from segmented OCT volumes were studied. After developing a method to maximize visualization of the posterior pole vasculature, a pilot test was carried out to evaluate the feasibility of grading the resulting images for plus, pre-plus, or neither. A stratified random sample of 17 imaging sessions from 15 eyes of 13 infants from the BabySTEPS cohort was selected. For two eyes with plus or pre-plus on clinical examination, images from two imaging sessions for each eye were included, with the goal of yielding an enriched sample with an approximately equal number of imaging sessions with plus, pre-plus, or neither on clinical examination. Images captured from eyes after ROP treatment were excluded.

The OCT volumes were segmented using the Duke OCT Retinal Analysis Program Marking Code (DOCTRAP) v63.9, and Pediatric v1.2 (MATLAB R2017b, MathWorks, Natick, MA). The DOCTRAP software contains retinal layer segmentation algorithms that were developed based on graph theory and dynamic programming, in which images are represented as a graph of nodes that are connected by weighted edges. The algorithms vary the values of the weights based on the layer boundary of interest. The shortest weighted path from one side of the image to the other results in a segmented layer boundary.

Several approaches were explored to extract en face vascular information from segmented OCT volumes to improve on the OCT-generated conventional retina view images, which originate from the mean pixel intensity of data from the entire cross-sectional scan. For example, approaches included extracting enface images from the inner or outer retinal layers, or from volumetric data centered around individual retinal layers, as shown in FIG. 6.

Figure 6:
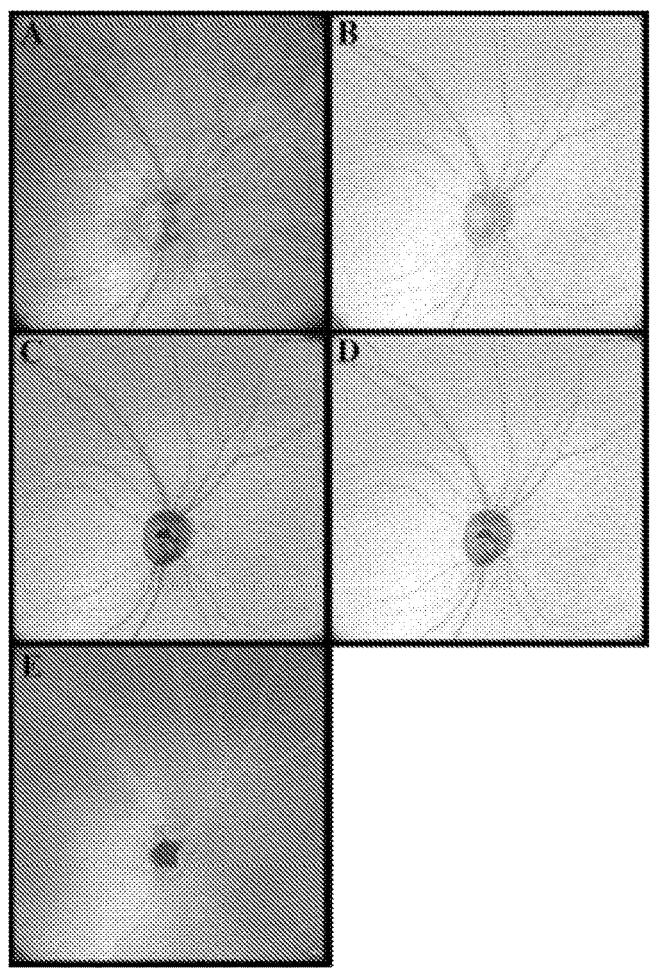
FIG. 6 shows en face OCT images taken from a preterm infant extracted using different parameters.

FIG. 6 illustrates enface OCT images taken from a preterm infant extracted using different parameters. Referring to FIG. 6, the following en face OCT images were taken: (A) Mean pixel intensity from the entire cross-sectional scan (resulting in the "conventional retina view OCT image"); (B) maximum pixel intensity from the entire volume; (C) mean pixel intensity from around the RPE (resulting in the RVSV-OCT); (D) maximum pixel intensity from around the RPE; (E) mean pixel intensity from the internal limiting membrane to the outer boundary of the inner nuclear layer (representing the inner retina). The RVSV-OCT (C) best illustrates retinal vessel patterns, as the conventional retina view image (A) has distracting choroidal vasculature, the two maximum intensity images (B and D) demonstrate retinal vessel washout, and the inner retinal layer image (E) features low vessel contrast.

Figure 7:
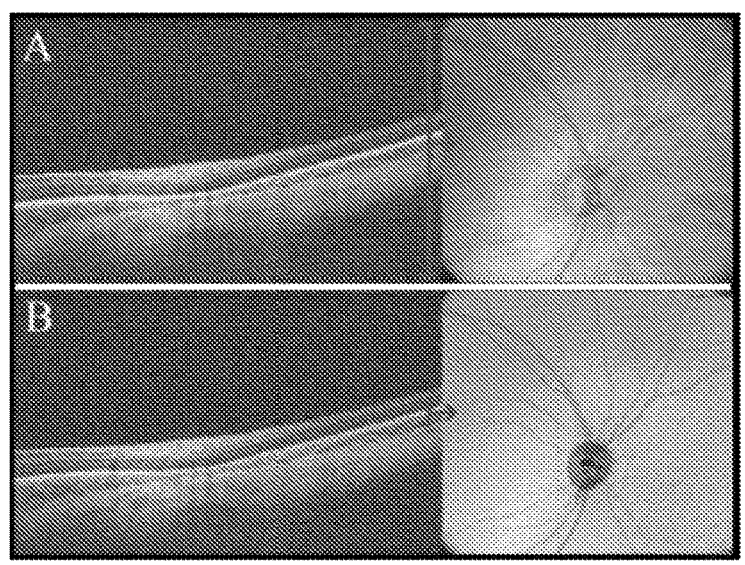
FIG. 7 shows en face images extracted from cross-sectional OCT scans.

From this preliminary exploration, the described RVSV-OCT visualization was selected. The RVSV-OCT images were extracted from the mean pixel intensity of volumetric data restricted to a narrow axial window bracketed around the RPE, for the purpose of enhancing the view of retinal vessel shadows and removing choroidal patterns, as shown in FIG. 7. Thus, the RVSV-OCT images were centered on vessel shadowing at the level of the RPE.

FIG. 7 illustrates en face images extracted from cross-sectional OCT scans. Image (A) illustrates a conventional retina view image extracted from the entire OCT volume; and image (B) illustrates an RVSV-OCT image extracted from volumetric data bracketed around the autosegmented level of the RPE. Graders reported that compared with conventional retina view image, RVSV-OCT images eliminated potentially distracting choroidal vasculature and improved visibility and distinctness of retinal vessels, as shown in FIG. 7.

RVSV-OCT images were compared to the OCT-generated conventional retina view images. Images were loaded into previously validated, commercially available automontage software (i2k Retina; DualAlign, Inc., Clifton Park, NY). The software created a single conventional retina view montage and a single RVSV-OCT montage for each eye; in most eyes, the two montages had identical fields of view. However, in five eyes the software automontaged more RVSV-OCT images than conventional retina view images. These extra images were removed from the RVSV-OCT montage to ensure the same number of images were included in the two montages, creating equal fields of view for the reviewers.

Three fellowship-trained pediatric ophthalmologists who actively perform ROP screening (SFF, SFG, and SGP) reviewed and graded the OCT montages independently. The graders were sent three separate electronic slideshows. The first slideshow presented one slide per imaging session with the conventional retina view and RVSV-OCT montages side-by-side, and asked graders to indicate their preferred montage (conventional retina view or RVSV-OCT) for grading of posterior pole vasculature. The second slideshow presented a reference slide with standardized photographs of plus and pre-plus disease, taken from the ICROP Revisited, on the first slide, followed by RVSV-OCT montages, one per slide, and graders were asked to grade the RVSV-OCT montages for plus, pre-plus, or neither based on the provided reference slide. The third slideshow presented all 17 RVSV-OCT montages on a single slide, and graders were asked to rank each RVSV-OCT montage for ROP vascular disease severity relative to the other RVSV-OCT montages (with a ranking of 1 indicating least severe, and 17 indicating most severe). Reviewers graded the montages as "ungradable" if the images did not completely capture the optic disc and have 2 or more quadrants, each with 1 or more vessels visible for a length of 1 or more optic disk diameter, or approximately 1.5 mm. Graders were masked to clinical examination diagnoses and other graders' gradings.

Statistical analysis was performed using R v3.6.1 (R Foundation for Statistical Computing, Vienna, Austria). The sensitivity and specificity of using RVSV-OCT grading for detecting plus disease present on clinical examination (reference standard) was calculated by binarizing the grades as "plus" or "not plus". Intergrader agreement of plus, pre-plus, or neither grades were assessed using the weighted κ statistic, and intergrader agreement was assessed on relative vascular disease severity rankings using the intraclass correlation coefficient (ICC). Both the weighted κ and ICC were interpreted using a standardized scale: 0 to 0.4, poor; 0.4 to 0.59, fair; 0.6 to 0.74, good; and 0.75 to 1.0, excellent. The median relative vascular disease severity ranking for the three graders was used as a summary (consensus) reference score for relative vascular disease severity.

In a post hoc secondary analysis of color photographs versus RVSV-OCT montages, fundus photographs (RetCam; Natus Medical, Inc., Pleasanton, CA) acquired the same day as the BabySTEPS OCT imaging session from the clinical record were collected. Six imaging sessions from five eyes of three infants that included both fundus photography and OCT imaging were included. Two eyes from the main study described earlier were among these five eyes with color photographs; however, the color photographs and OCT images were acquired from different imaging sessions than were included in the main study described earlier. For one eye, images were included from two imaging sessions in this analysis, with the goal of maximizing sample size. The SS-OCT volumes were autosegmented and extracted, and the RVSV-OCT images were automontaged, as described earlier. Unlike the main study, RVSV-OCT images were not removed from the automontage and manually added peripheral images to maximize montage field of view. A set of three RetCam photographs was selected for each visit to maximize total field of view, and manually adjusted a duplicate set for brightness and contrast to maximize vessel visibility. In a grading session separate from the main study as described earlier, the graders first evaluated the RVSV-OCT montages for fundus pigmentation (blond, medium, or dark). The graders then answered the question: "Does fundus pigmentation impact image gradeability for plus, pre-plus, or neither?" Next, the graders repeated their evaluation of pigmentation and its impact on gradeability on the sets of uncorrected and corrected fundus photographs. Finally, the graders indicated their preference for either fundus photographs or RVSV-OCT montages for grading for the presence of plus, pre-plus, or neither.

Results

From the BabySTEPS cohort, 17 imaging sessions from 15 eyes of 13 infants were included in the conventional retina view versus RVSV-OCT analysis. At the time of clinical examination, seven had plus disease, four had pre-plus, and six had neither; with regard to fundus pigmentation, 11 were classified as blond, five as medium, and one as dark. Mean gestational age was 26.1 (SD=2.8) weeks; mean birth weight was 742.1 (SD=242.4) grams; mean postmenstrual age at imaging was 38.3 (SD=4.7) weeks.

Figure 8:
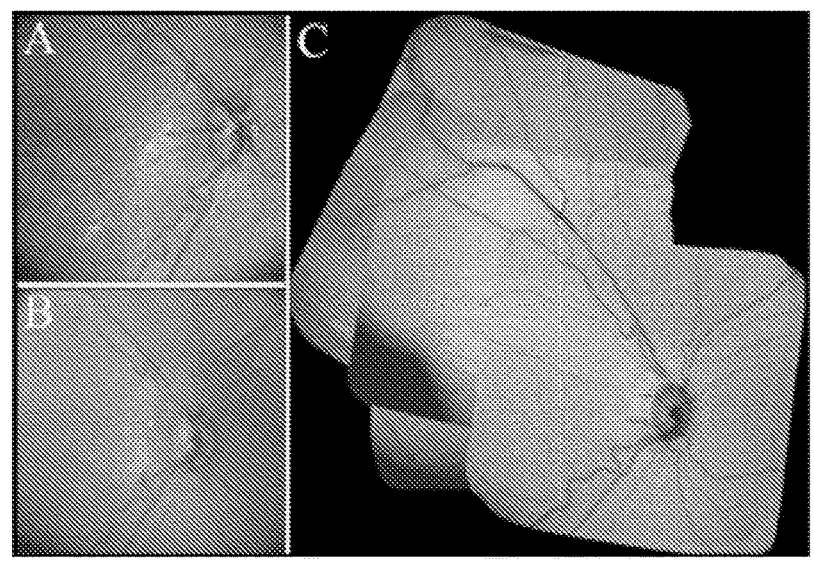
FIG. 8 shows a comparison of enface OCT images taken at the bedside of the same preterm eye.
Figure 9:
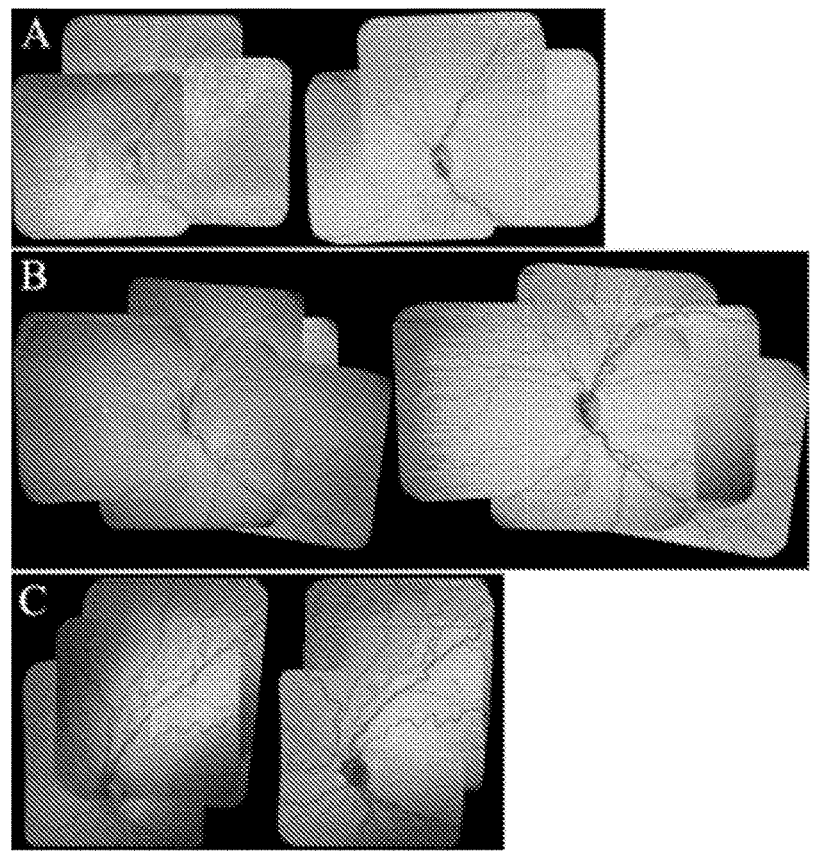
FIG. 9 shows montaged conventional retina view OCT images and RVSV-OCT images from investigational, bedside OCT of preterm eyes with neither plus nor pre-plus; pre-plus; and plus disease.

The three pediatric ophthalmologist graders preferred the RVSV-OCT montage over the conventional retina view montage for grading posterior pole vascular severity in $36/51$ (71%) gradings (17 images times three graders, equals 51 total gradings), and the majority of graders preferred the RVSV-OCT montage in $11/17$ (65%) cases. Graders frequently mentioned improved retinal vessel visualization on RVSV-OCT montage compared with the conventional retina view, citing "more distinct retinal vessels" (n=$15/51$), "crisper retinal vessel margins" (n=$8/51$), "better retinal vessel contrast" (n=$5/51$), "more retinal vessels visible" (n=$3/51$), and "absence of distracting choroidal vasculature" (n=$2/51$), as shown in FIGS. 7-9. When graders preferred the conventional retina view montage over the RVSV-OCT montage, they cited decreased vessel dilation (n=$7/51$) or presence of artifact (n=$5/51$) in the RVSV-OCT.

FIG. 8 illustrates a comparison of en face OCT images taken at the bedside of the same preterm eye. Referring to FIG. 8, image (A) illustrates a commercial spectral domain OCT (Envisu C2300, Leica Microsystems); image (B) illustrates a conventional retina view image from investigational, high-speed SS-OCT; and image (C) illustrates RVSV-OCT montage. The RVSV-OCT montage features improved pixel density, retinal vessel pattern visualization, and field of view compared with the commercial image.

FIG. 9 illustrates montaged conventional retina view OCT images and RVSV-OCT images from investigational, bedside OCT of preterm eyes with neither plus nor pre-plus; pre-plus; and plus disease. Referring to FIG. 9, the montaged conventional retina view OCT images are shown on the left and the RVSV-OCT images are shown on the right. (A) illustrates preterm eyes with neither plus nor pre-plus; (B) illustrates preterm eyes with pre-plus; and (C) illustrates preterm eyes with plus disease. In FIG. 9, horizontal black lines in RVSV-OCT images represent artifact due to autosegmentation errors.

Graders found $15/17$ (88%) RVSV-OCT montages gradable for plus disease, pre-plus, or neither and all 17 montages rankable for relative ROP vascular disease severity. Of the two ungradable montages, one (ranked $11/17$ on the consensus reference score for vascular disease severity) was deemed ungradable by one grader, and one (ranked $8/17$) was deemed ungradable by two graders.

When each individual graded plus, pre-plus, neither, or ungradable using RVSV-OCT, they agreed with the reference standard (diagnosis on clinical examination) in $36/51$ (710%) gradings, as shown in FIG. 10.

FIG. 10 illustrates RVSV-OCT images ordered by the median (consensus) relative vascular disease severity ranking from least (1) to most (17) severe, with corresponding clinical examination grades and plus (P), pre-plus (PP), or neither (N) RVSV-OCT grades for each grader. U, ungradable. Shading indicates disagreement with clinical examination grade. Each grader had a unique cutoff point for the diagnosis of pre-plus (lighter line) and plus (darker line) disease.

The three graders together agreed with the reference standard on $9/17$ (53%) images; this included all six images of eyes with neither plus nor pre-plus on clinical examination, as shown in FIG. 10. When the 51 grades were instead binarized as "plus" or "not plus" (which included pre-plus, neither plus nor pre-plus, and ungradable), the sensitivity and specificity for detecting plus disease were $11/21$ (52.4%) and $28/30$ (93.3%), respectively. Of the 10 instances of missed plus disease, nine were graded as pre-plus and one was deemed ungradable; no eyes with plus disease on clinical examination were graded as neither plus nor pre-plus, as shown in FIG. 10.

Among the 15 RVSV-OCT montages that all three graders found to be gradable for plus, pre-plus, or neither, graders agreed with each other in $35/45$ (78%) grading pairs. Overall, intergrader agreement for plus, pre-plus, or neither was good (weighted κ=0.67; 95% confidence interval, 0.42-0.86). In contrast, relative ROP vascular disease severity rankings exhibited excellent intergrader agreement (ICC 0.98; 95% confidence interval, 0.96-0.99). The relative severity rankings also correlated well with plus, pre-plus, or neither grades on clinical examination, as shown in FIG. 11.

FIG. 11 illustrates consensus (median) relative vascular disease severity rankings for 17 RVSV-OCT montages, from least (1) to most severe (17), versus individual grader rankings. Referring to FIG. 11, relative vascular disease severity rankings exhibited excellent intergrader agreement (ICC 0.98) and correlated well with plus, pre-plus, or neither diagnosis on clinical examination.

In the post hoc review, grader comments regarding RVSV-OCT montage quality and vessel contrast did not appear to be impacted by fundus pigmentation, which inspired the post hoc pigmentation analysis. For this post hoc analysis of color photographs versus RVSV-OCT, six imaging sessions from five eyes of three infants were included. At time of clinical examination, two had plus disease, two had pre-plus disease, and two had neither; and three had blond pigmentation, and three had dark pigmentation. Graders correctly identified fundus pigmentation in $2/18$ (11%) gradings using RVSV-OCT montages compared with $14/18$ (78%) gradings using sets of fundus photographs, as shown in FIG. 12.

Figure 12:
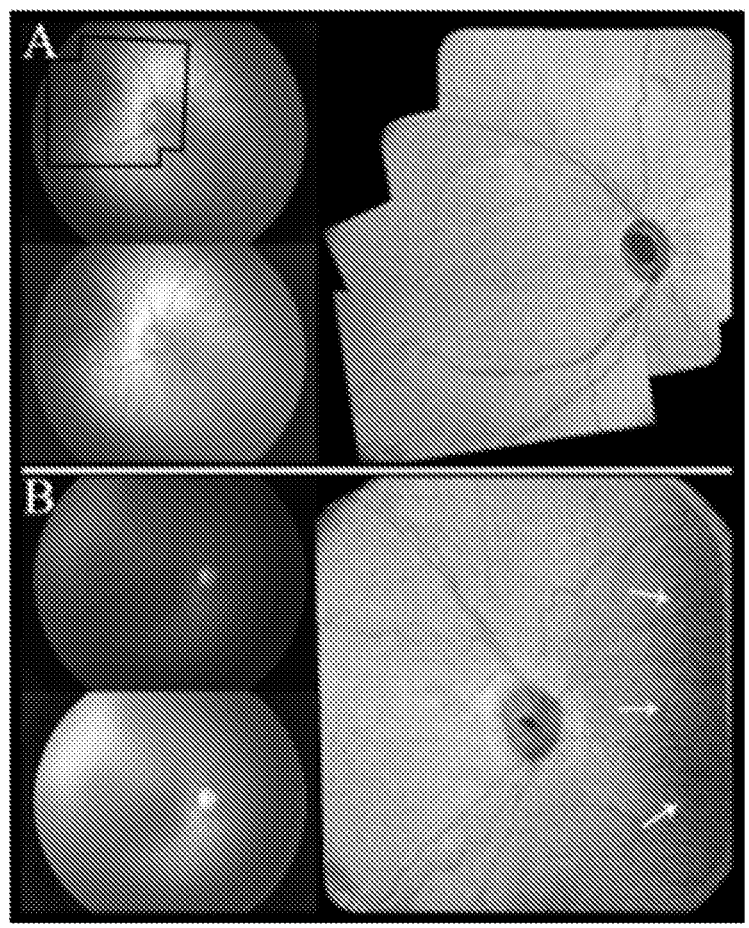
FIG. 12 shows a comparison of fundus photographs and montaged RVSV-OCT images in preterm eyes with (A) blond and (B) dark fundus pigmentation.

FIG. 12 illustrates a comparison of fundus photographs and montaged RVSV-OCT images in preterm eyes with (A)

blond and (B) dark fundus pigmentation. Referring to FIG. 12, fundus pigmentation appeared to impact retinal vessel visualization in the unadjusted (top left) and brightness- and contrast-adjusted (bottom left) fundus photographs, but not in the RVSV-OCT (right). In the darkly pigmented eye, autosegmentation errors resulted in artifact in the nasal periphery of the RVSV-OCT (white arrows, B). Montaged RVSV-OCT field of view was smaller than that of a single fundus photograph (black outline, A).

Graders reported that fundus pigmentation impacted their ability to grade plus, pre-plus, or neither in 2/18 (11%) RVSV-OCT montages compared with 12/18 (67%) sets of fundus photographs. Graders preferred the RVSV-OCT montages for grading in 8/18 (44%) gradings and the majority of graders preferred RVSV-OCT montages for grading plus, pre-plus, or neither in 2/6 (33%) cases, citing clearer vessel visibility (n=5/18) or reduced glare (n=4/18). Graders preferred the fundus photographs for grading in 10/18 (56%) gradings and the majority of graders preferred fundus photographs for grading in 4/6 (67%) cases, citing greater field of view (n=6/18) or lack of apparent artifact (n=3/18). Despite varying preferences for RVSV-OCT versus fundus photograph for grading plus, pre-plus, or neither, all graders expressed comfort using either imaging modality for grading.

DISCUSSION

In the example implementation, a method for extracting two-dimensional en face RVSV-OCT images from structural OCT scans in preterm infants, a comparison of montaged RVSV-OCT to both conventional retina view OCT and wide-field fundus photographs, and the application of montaged RVSV-OCT for grading and ranking ROP posterior pole vascular disease by ophthalmologists were described. Montaged RVSV-OCT can provide improved grading of posterior pole vascular disease in a majority of cases and gradings than conventional retina view OCT. Further, fundus pigmentation does not appear to impact vessel visualization on RVSV-OCT, and ROP screeners can reliably and consistently rank relative posterior pole vascular disease severity for ROP using RVSV-OCT montages.

As previously described, the optimized RVSV-OCT images have several advantages over conventional retina view OCT images. The extraction of RVSV-OCT images exclusively from volumetric data around the autosegmented RPE can result in the elimination of distracting choroidal vasculature. The elimination of choroidal patterns can improve visualization of retinal vessels, and is advantageous for grading by clinicians. By extracting volumetric data around the RPE, choroidal pigment can also be eliminated, which develops at approximately 34 weeks post-menstrual age and has been shown to impact OCT scan depth and quality. In some cases, the impact may explain graders' inability to identify fundus pigmentation on RVSV-OCT images. However, the preponderance of blond fundi in this pilot study (9/17) may limit the generalizability of this finding.

In this example implementation, the selective extraction procedure is enabled by custom infant-specific autosegmentation software that accurately delineates retinal layers in preterm eyes, despite a range of post-menstrual ages and stages of retinal development. The autosegmentation process also produces retinal thickness data across the volume. This provides a measure of axial tortuosity and has been one factor used in the VASO. In some cases, thickness map data may be combined with RVSV-OCT images. Additionally, automontage can combine individual RVSV-OCT images, which have a relatively small field of view because of the noncontact nature of the investigational system, into a single montage that covers a larger area of the posterior pole. The montaged RVSV-OCT images appear to be a significant improvement over individual enface OCT images currently available at the bedside.

The investigational SS-OCT system used to capture these RVSV-OCT images also overcomes several limitations of current bedside imaging systems. The high capture speed of the 200 kHz investigational OCT system maximizes data acquisition during scan periods that are necessarily limited in awake, nonfixating infants. This enables the creation of RVSV-OCT images with greater pixel density, and therefore higher quality, than commercial en face OCT images. Second, the use of a noncontact probe enables the capture of retinal vessel patterns, potentially useful for ROP screening, without retinal vessel changes or the stress response that can be created by a contact fundus camera.

Using RVSV-OCT montages can help in ranking relative posterior pole vascular disease severity in preterm infants at risk for ROP. All 17 RVSV-OCT montages were rankable for relative vascular disease severity, and the rankings featured excellent intergrader agreement and correlated well with plus, pre-plus, or neither diagnoses on clinical examination. RVSV-OCT images may therefore have sufficient retinal vessel visualization for the reliable demonstration of relative ROP vascular disease severity in preterm eyes.

It should be noted that the example implementation did not incorporate optimizations of the scans for enface viewing. Isotropic scan protocols may improve retinal vessel visibility and graders' ability to detect posterior pole vascular disease on RVSV-OCT images. Similarly, the RVSV-OCT capture was not optimized for automontaging, which requires overlap between adjacent enface images. This may have limited the number of images automontaged and the field of view of the resulting RVSV-OCT montage, which was smaller than that of a single wide-field fundus photograph. More consistent overlap between adjacent scans and capture of the peripheral retina may improve the utility of RVSV-OCT montages, as increased field of view contributed to graders' preference for fundus photographs over RVSV-OCT and has been shown to improve the reliability of plus disease diagnoses.

Certain aspects of the invention provide the following non-limiting embodiments:

Example 1. A method comprising: receiving a volumetric optical coherence tomography (OCT) scan of a patient; segmenting the volumetric OCT scan to determine layer boundaries; delineating a boundary of interest based on the determined layer boundaries of the segmented volumetric OCT scan; extracting en face vascular information from the segmented volumetric OCT scans to create a retinal vessel shadow view (RVSV)-OCT image by: determining a first offset from the boundary of interest and a second offset from the boundary of interest; extracting volumetric data from an area between the first offset and the second offset to create a three-dimensional volume; and identifying a two-dimensional surface from the three-dimensional volume, the two-dimensional surface being the RVSV-OCT image; and providing the RVSV-OCT image for analysis.

Example 2. The method of example 1, wherein identifying the two-dimensional surface from the three-dimensional volume comprises calculating a mean pixel intensity of the three-dimensional volume.

Example 3. The method of examples 1 or 2, wherein the layer boundaries are retinal layer boundaries.

Example 4. The method of any of examples 1-3, wherein the patient is an infant, wherein the boundary of interest is Bruch's membrane, wherein the first offset is 20 microns above the Bruch's membrane and the second offset is 20 microns below the Bruch's membrane.

Example 5. The method of any of examples 1-3, wherein the patient is an adult, wherein the boundary of interest is a retinal pigment epithelium (RPE) layer, wherein the first offset is 10 microns above the RPE layer and the second offset is 10 microns below the RPE layer.

Example 6. The method of any of examples 1-5, wherein the volumetric OCT scan comprises radial scans, raster scans, or spiral scans.

Example 7. The method of any of examples 1-6, wherein the providing of the RVSV-OCT image for analysis comprises providing the RVSV-OCT image to a clinician device for clinician grading of the RVSV-OCT image.

Example 8. The method of any of examples 1-6, wherein the providing of the RVSV-OCT image for analysis comprises providing the RVSV-OCT image to an image processing system for extraction of at least one of vessel data or optic nerve data.

Example 9. The method of any of examples 1-6, wherein the providing of the RVSV-OCT image for analysis comprises providing the RVSV-OCT image to an artificial intelligence system or a machine learning system for analysis.

Example 10. The method of any of examples 1-9, wherein the segmenting of the volumetric OCT scans is based on an age of the patient.

Example 11. A system comprising: a processing system; a storage system; and instructions stored on the storage system that when executed by the processing system direct the processing system to at least: receive a volumetric optical coherence tomography (OCT) scan of a patient; segment the volumetric OCT scan to determine layer boundaries; delineate a boundary of interest based on the determined layer boundaries of the segmented volumetric OCT scan; extract enface vascular information from the segmented volumetric OCT scan to create a retinal vessel shadow view (RVSV)-OCT image by: determining a first offset from the boundary of interest and a second offset from the boundary of interest; extracting volumetric data from an area between the first offset and the second offset to create a three-dimensional volume; and identifying a two-dimensional surface from the three-dimensional volume, the two-dimensional surface being the RVSV-OCT image; and provide the RVSV-OCT image for analysis.

Example 12. The system of example 11, wherein the boundary of interest is Bruch's membrane or a retinal pigment epithelium layer.

Example 13. The system of examples 11 or 12, wherein the layer boundaries are retinal layer boundaries.

Example 14. The system of any of any of examples 11-13, wherein identifying the two-dimensional surface from the three-dimensional volume comprises calculating a mean pixel intensity of the three-dimensional volume.

Example 15. The system of any of examples 11-14, wherein the first offset is zero and the second offset is a location below the boundary of interest.

Example 16. A computer-readable storage medium having instructions stored thereon that, when executed by a processing system, perform a method comprising: receiving a volumetric optical coherence tomography (OCT) scan of a patient; segmenting the volumetric OCT scan to determine layer boundaries; delineating a boundary of interest based on the determined layer boundaries of the segmented volumetric OCT scan; extracting enface vascular information from the segmented volumetric OCT scan to create a retinal vessel shadow view (RVSV)-OCT image by: determining a first offset from the boundary of interest and a second offset from the boundary of interest; extracting volumetric data from an area between the first offset and the second offset to create a three-dimensional volume; and identifying a two-dimensional surface from the three-dimensional volume, the two-dimensional surface being the RVSV-OCT image; and providing the RVSV-OCT image for analysis.

Example 17. The medium of example 16, wherein the boundary of interest is Bruch's membrane or a retinal pigment epithelium layer.

Example 18. The medium of examples 16 or 17, wherein identifying the two-dimensional surface from the three-dimensional volume comprises calculating a mean pixel intensity of the three-dimensional volume.

Example 19. The medium of examples 16 or 18, wherein the layer boundaries are choroid layer boundaries.

Example 20. The medium of any of examples 16-19, wherein the first offset is a location above the boundary of interest and the second offset is zero.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. A method comprising:
   receiving a volumetric optical coherence tomography (OCT) scan of a patient;
   segmenting the volumetric OCT scan to determine layer boundaries;
   delineating a boundary of interest based on the determined layer boundaries of the segmented volumetric OCT scan;
   extracting en face vascular information from the segmented volumetric OCT scans to create a retinal vessel shadow view (RVSV)-OCT image by:
   determining a first offset from the boundary of interest and a second offset from the boundary of interest;
   extracting volumetric data from an area between the first offset and the second offset to create a three-dimensional volume; and
   identifying a two-dimensional surface from the three-dimensional volume, the two-dimensional surface being the RVSV-OCT image; and
   providing the RVSV-OCT image for analysis.

2. The method of claim 1, wherein identifying the two-dimensional surface from the three-dimensional volume comprises calculating a mean pixel intensity of the three-dimensional volume.

3. The method of claim 1, wherein the layer boundaries are retinal layer boundaries.

4. The method of claim 1, wherein the patient is an infant, wherein the boundary of interest is Bruch's membrane, wherein the first offset is 20 microns above the Bruch's membrane and the second offset is 20 microns below the Bruch's membrane.

5. The method of claim 1, wherein the patient is an adult, wherein the boundary of interest is a retinal pigment epithelium (RPE) layer, wherein the first offset is 10 microns above the RPE layer and the second offset is 10 microns below the RPE layer.

6. The method of claim 1, wherein the volumetric OCT scan comprises radial scans, raster scans, or spiral scans.

7. The method of claim 1, wherein the providing of the RVSV-OCT image for analysis comprises providing the RVSV-OCT image to a clinician device for clinician grading of the RVSV-OCT image.

8. The method of claim 1, wherein the providing of the RVSV-OCT image for analysis comprises providing the RVSV-OCT image to an image processing system for extraction of at least one of vessel data or optic nerve data.

9. The method of claim 1, wherein the providing of the RVSV-OCT image for analysis comprises providing the RVSV-OCT image to an artificial intelligence system or a machine learning system for analysis.

10. The method of claim 1, wherein the segmenting of the volumetric OCT scans is based on an age of the patient.

11. A system comprising:
a processing system;
a storage system; and
instructions stored on the storage system that when executed by the processing system direct the processing system to at least:
receive a volumetric optical coherence tomography (OCT) scan of a patient;
segment the volumetric OCT scan to determine layer boundaries;
delineate a boundary of interest based on the determined layer boundaries of the segmented volumetric OCT scan;
extract enface vascular information from the segmented volumetric OCT scan to create a retinal vessel shadow view (RVSV)-OCT image by:
determining a first offset from the boundary of interest and a second offset from the boundary of interest;
extracting volumetric data from an area between the first offset and the second offset to create a three-dimensional volume; and
identifying a two-dimensional surface from the three-dimensional volume, the two-dimensional surface being the RVSV-OCT image; and
provide the RVSV-OCT image for analysis.

12. The system of claim 11, wherein the boundary of interest is Bruch's membrane or a retinal pigment epithelium layer.

13. The system of claim 11, wherein the layer boundaries are retinal layer boundaries.

14. The system of claim 11, wherein identifying the two-dimensional surface from the three-dimensional volume comprises calculating a mean pixel intensity of the three-dimensional volume.

15. The system of claim 11, wherein the first offset is zero and the second offset is a location below the boundary of interest.

16. A non-transitory computer-readable storage medium having instructions stored thereon that, when executed by a processing system, perform a method comprising:
receiving a volumetric optical coherence tomography (OCT) scan of a patient;
segmenting the volumetric OCT scan to determine layer boundaries;
delineating a boundary of interest based on the determined layer boundaries of the segmented volumetric OCT scan;
extracting en face vascular information from the segmented volumetric OCT scan to create a retinal vessel shadow view (RVSV)-OCT image by:
determining a first offset from the boundary of interest and a second offset from the boundary of interest;
extracting volumetric data from an area between the first offset and the second offset to create a three-dimensional volume; and
identifying a two-dimensional surface from the three-dimensional volume, the two-dimensional surface being the RVSV-OCT image; and
providing the RVSV-OCT image for analysis.

17. The medium of claim 16, wherein the boundary of interest is Bruch's membrane or a retinal pigment epithelium layer.

18. The medium of claim 16, wherein identifying the two-dimensional surface from the three-dimensional volume comprises calculating a mean pixel intensity of the three-dimensional volume.

19. The medium of claim 16, wherein the layer boundaries are choroid layer boundaries.

20. The medium of claim 16, wherein the first offset is a location above the boundary of interest and the second offset is zero.

* * * * *